US010393666B2

(12) United States Patent
Moretti et al.

(10) Patent No.: US 10,393,666 B2
(45) Date of Patent: Aug. 27, 2019

(54) METHODS, DEVICES, SYSTEMS, AND COMPOSITIONS FOR DETECTING GASES

(71) Applicant: Respirion, LLC, Winston Salem, NC (US)

(72) Inventors: Eugene W. Moretti, Durham, NC (US); Robert Lavin Wood, Cary, NC (US); Allan Bruce Shang, Wake Forest, NC (US); Steven S. Yauch, Clayton, NC (US)

(73) Assignee: RESPIRION, LLC, Winston Salem, NC (US)

( * ) Notice: Subject to any disclaimer, the term of this patent is extended or adjusted under 35 U.S.C. 154(b) by 633 days.

(21) Appl. No.: 13/796,593

(22) Filed: Mar. 12, 2013

(65) Prior Publication Data

US 2013/0259749 A1    Oct. 3, 2013

Related U.S. Application Data

(63) Continuation-in-part of application No. 13/609,024, filed on Sep. 10, 2012.

(60) Provisional application No. 61/609,603, filed on Mar. 12, 2012.

(51) Int. Cl.
   G01N 21/78    (2006.01)
   A61B 5/00    (2006.01)
   A61B 5/083    (2006.01)

(52) U.S. Cl.
   CPC ......... *G01N 21/783* (2013.01); *A61B 5/0836* (2013.01); *A61B 5/742* (2013.01); *Y10T 436/204998* (2015.01)

(58) Field of Classification Search
   CPC .. G01N 31/22; G01N 21/6428; G01N 1/2273; G01N 21/8483; G01N 21/783; G01N 27/126; G01N 33/4972; G01N 33/98; G01N 7/04; G01N 27/12
   See application file for complete search history.

(56) References Cited

U.S. PATENT DOCUMENTS

| 4,691,701 A | 9/1987 | Williams |
| 4,728,499 A | 3/1988 | Fehder |
| 4,760,250 A | 7/1988 | Loeppert |
| 4,790,327 A | 12/1988 | Despotis |

(Continued)

FOREIGN PATENT DOCUMENTS

| JP | 06-249850 | 9/1994 |
| JP | 3322902 B2 | 6/2002 |

(Continued)

OTHER PUBLICATIONS

International Preliminary Report on Patentability Corresponding to International Application No. PCT/US2013/030505; dated Sep. 16, 2014.

(Continued)

*Primary Examiner* — Lyle Alexander
*Assistant Examiner* — Dwan A Gerido
(74) *Attorney, Agent, or Firm* — NK Patent Law

(57) ABSTRACT

A method of monitoring a respiratory stream can be provided by monitoring color change of a color change material to determine a CO2 level of the respiratory stream in contact with the color change material by emitting visible light onto the color change material. Related devices, systems, and compositions are also disclosed.

21 Claims, 25 Drawing Sheets

(56) References Cited

U.S. PATENT DOCUMENTS

| | | | |
|---|---|---|---|
| 4,897,999 A | 2/1990 | Varney | |
| 4,928,687 A | 5/1990 | Lampotang et al. | |
| 4,945,918 A | 8/1990 | Abernathy | |
| 4,994,117 A * | 2/1991 | Fehder | 436/133 |
| 5,005,572 A | 4/1991 | Raemer et al. | |
| 5,124,129 A | 6/1992 | Riccitelli et al. | |
| 5,156,159 A | 10/1992 | Lampotang et al. | |
| 5,197,464 A | 3/1993 | Babb et al. | |
| 5,261,415 A | 11/1993 | Dussault | |
| 5,279,289 A | 1/1994 | Kirk | |
| 5,375,592 A | 12/1994 | Kirk et al. | |
| 5,432,061 A | 7/1995 | Berndt et al. | |
| 5,456,249 A | 10/1995 | Kirk | |
| 5,468,451 A | 11/1995 | Gedeon | |
| 5,517,985 A | 5/1996 | Kirk et al. | |
| 5,679,884 A | 10/1997 | Kirk | |
| 5,714,121 A | 2/1998 | Alderete et al. | |
| 5,749,358 A | 5/1998 | Good et al. | |
| 5,857,460 A | 1/1999 | Popitz | |
| 6,085,576 A | 7/2000 | Sunshine et al. | |
| 6,241,873 B1 | 6/2001 | Namba et al. | |
| 7,017,578 B2 | 3/2006 | Tresnak et al. | |
| 7,140,370 B2 | 11/2006 | Tresnak et al. | |
| 7,171,312 B2 | 1/2007 | Steinthal et al. | |
| 7,578,971 B2 | 8/2009 | Ratner et al. | |
| 7,628,907 B2 | 12/2009 | Gu et al. | |
| 7,992,561 B2 | 8/2011 | Baker, Jr. et al. | |
| 8,002,712 B2 | 8/2011 | Meka et al. | |
| 8,109,272 B2 | 2/2012 | Baker, Jr. et al. | |
| 8,128,574 B2 | 3/2012 | Baker, Jr. et al. | |
| 2002/0103444 A1 | 8/2002 | Ricciardelli | |
| 2007/0048181 A1 | 3/2007 | Chang et al. | |
| 2008/0072905 A1* | 3/2008 | Baker et al. | 128/204.23 |
| 2008/0075633 A1 | 3/2008 | Ostrowski et al. | |
| 2010/0078030 A1 | 4/2010 | Colburn | |
| 2010/0305464 A1 | 12/2010 | Ratner | |
| 2010/0310425 A1 | 12/2010 | Piper | |

FOREIGN PATENT DOCUMENTS

| | | |
|---|---|---|
| JP | 2003-315264 | 11/2003 |
| WO | WO 2008/005907 A2 | 1/2008 |

OTHER PUBLICATIONS

Notification of Transmittal of the International Search Report and the Written Opinion of the International Searching Authority, or the Declaration in corresponding PCT Application No. PCT/US2013/030505 dated Aug. 14, 2013 (18 pages).

Extended European Search Report corresponding to European Patent Application No. 13761333.7 (7 pages) (dated Dec. 4, 2015).

Office Action corresponding to related Japanese Application No. 2015-500515 (7 pages) (dated Jan. 24, 2017).

* cited by examiner

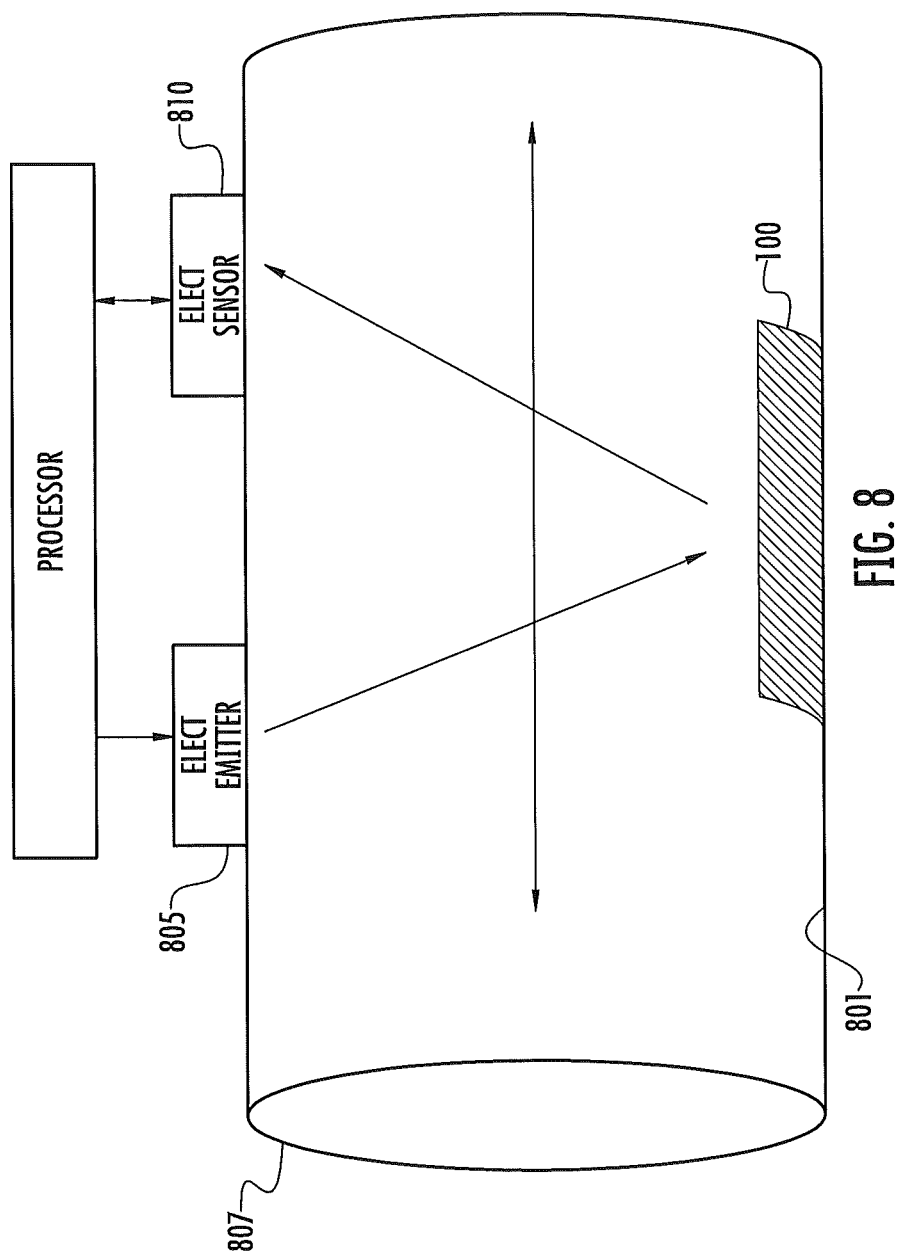

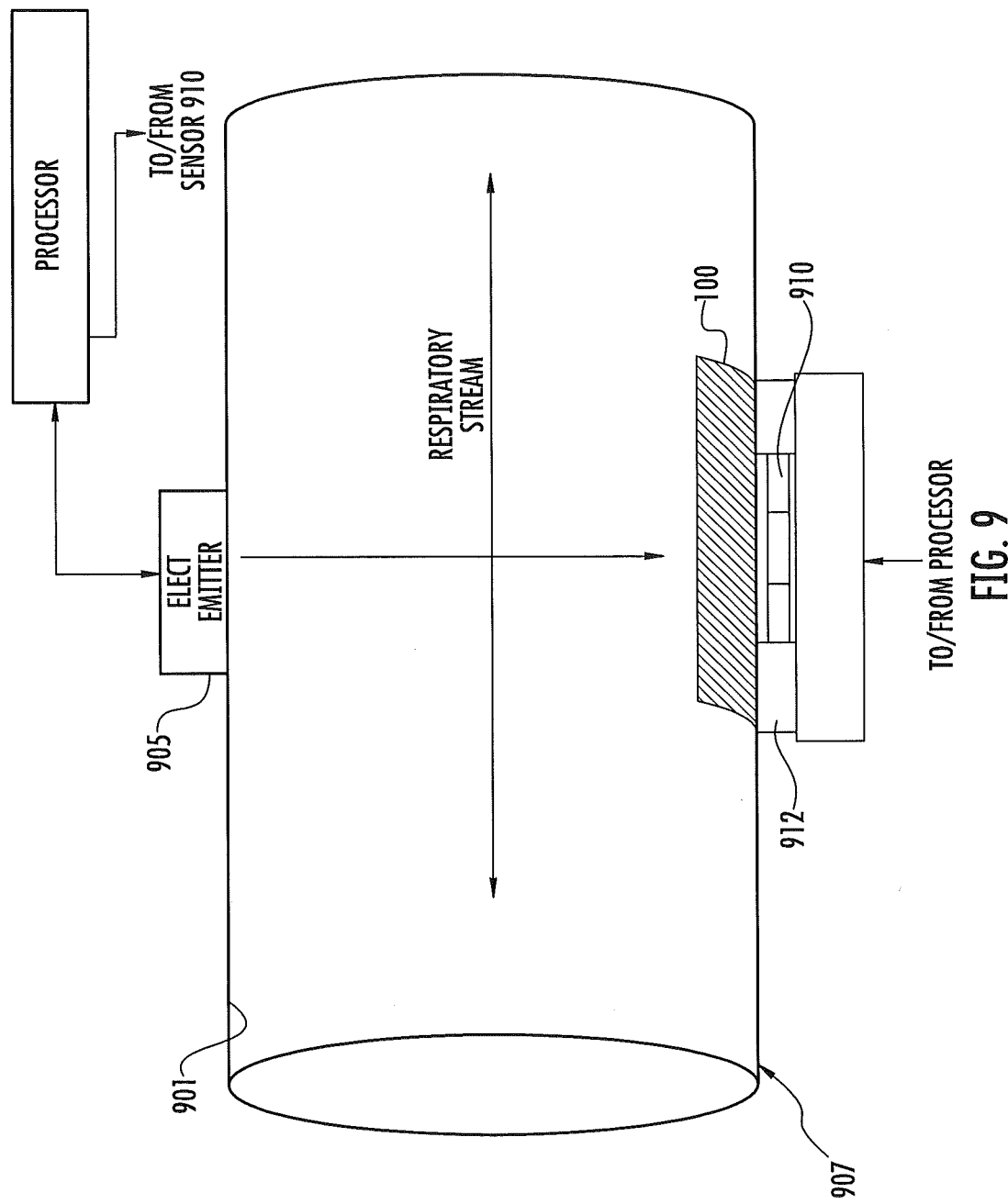

METHODS, DEVICES, SYSTEMS, AND COMPOSITIONS FOR DETECTING GASES

CROSS-REFERENCE TO RELATED APPLICATION

This Application is a continuation-in-part of and claims priority to U.S. patent application Ser. No. 13/609,024, entitled Methods, Devices, Systems, and Compositions for Detecting Gases, filed on Sep. 10, 2012, and claims the benefit of and priority to U.S. Provisional Patent Application No. 61/609,603, entitled Methods and Apparatus for Detecting Carbon Dioxide Levels, filed on Mar. 12, 2012, the disclosures of each of which are entirely incorporated herein by reference.

FIELD OF INVENTION

The present invention relates to the measurement of gas levels, and more specifically, to measuring respiratory gases.

BACKGROUND

First responders, respiratory therapists and critical care personnel perform emergency laryngoscopy and intubation under a variety of conditions and under great duress. Securing a viable and protected airway is one of the paramount steps of a successful resuscitation. Often times airway manipulation and instrumentation are performed in suboptimal conditions by inexperienced or lightly trained personnel. These procedures have the potential for disaster if they result in an esophageal intubation, causing hypoxia, anoxia, and cardiopulmonary arrest if allowed to continue unrecognized.

Capnography, the measurement of $CO_2$ in expired or respirated gases has been commonly used in the operating room setting for several years. Capnography readily identifies situations that can lead to hypoxia if left undetected and dealt with. For example, one use of a $CO_2$ measuring device is to confirm proper endotracheal tube placement during general anesthesia. By identifying improper placement, the provider can then rectify potential hypoxic conditions before hypoxia can actually lead to severe brain damage. Recently the use of capnography has been extended outside of the operating room arena to include emergency rooms, intensive care units, endoscopic suites, radiographic suites and first responders at catastrophic events (e.g. motor vehicle or industrial accidents).

The current standard of care for collect endotracheal tube placement calls for multiple methods of confirmation, one of which could be a carbon dioxide detector. Typically, however, the method used to confirm proper placement is a capnographic waveform monitor. Unfortunately, this monitor may be a complex electronic device only capable of functioning in highly controlled environments, such as an operating room. In many cases, these devices are not available, suited, or adapted for the location in which these procedures may be necessary.

Other types of endotrachael tube placement confirmation may be a disposable colorimetric detector. This type of detector confirms the presence of $CO_2$ via a visible color change in equipment or test strip when exposed to exhaled gases containing $CO_2$. This device detects $CO_2$ via a chemical reaction which causes a color shift in a reagent containing substrate contained within the device.

Colorimetric detectors are generally useful as qualitative indicators of the presence or absence of $CO_2$. Various methods have been disclosed for quantitative detection of $CO_2$ in respired gas samples. However limitations of these devices may be that they may not provide useful feedback during various patient procedures such as cardiopulmonary resuscitation and/or ventilation. These simple detectors may not add value to patient outcomes beyond informing a simple gate decision of whether $CO_2$ is present or absent in respiratory gases.

$CO_2$ concentration at the end of a breath can represent the end tidal carbon dioxide concentration ($PETCO_2$). Decreases in cardiac output and pulmonary blood flow can result in decreases in $PETCO_2$. Correspondingly, increases in cardiac output and pulmonary blood flow result in better perfusion of the alveoli and a rise in $PETCO_2$. The relationship between cardiac output and $PETCO_2$ has been determined to be logarithmic. Therefore capnography can detect the presence of pulmonary blood flow even in the absence of major pulses, and it can indicate changes in pulmonary blood flow caused by alterations in cardiac rhythm. Initial data samples reveal that the $PETCO_2$ may correlate with coronary perfusion pressure. This correlation between perfusion pressure and $PETCO_2$ is likely to be secondary to the relationship between $PETCO_2$ and cardiac output.

Capnographic measurements have been evaluated to predict outcomes in cardiac arrest. A study involving 127 patients revealed that only one patient with a $PETCO_2$ less than 10 mm Hg during resuscitation survived to hospital discharge. In another prospective investigation involving 139 adult victims of out-of-hospital, non-traumatic cardiac arrest, no patient with an average $PETCO_2$ less than 10 mm Hg upon initial resuscitation survived. The analysis of these studies concluded that $PETCO_2$ can be correlated with resuscitation and outcome in cardiopulmonary resuscitation (CPR). Moreover, another application of capnography in this setting is to provide feedback to optimize chest compressions during CPR. Monitoring $PETCO_2$ may detect inadequate chest compressions secondary to fatigue that could result in a sub-optimal cardiac output.

Capnography is gaining increasing acceptance during the resuscitation of trauma victims. $PETCO_2$ is a marker of traumatic physiology, as it reflects changes in cardiac output. Recently a study involving 191 blunt trauma patients revealed that $PETCO_2$ may be of value in predicting outcome from major trauma. In this investigation only 5% of patients with a $PETCO_2$ less than 10 mm Hg survived to hospital discharge. Other studies have shown capnography to be of value in providing optimum ventilation in prehospital major trauma victims. Patients monitored using capnography had a statistically significant higher incidence of normoventilation (normal $CO_2$ levels in the blood) compared to those who were not managed with capnography (63.2% vs. 20% p<0.0001).

Some previous $CO_2$ detectors make use of an electrochemical detection device referred to collectively as "chemiresistors". Such devices respond to the absorption of target chemical species by undergoing a change in ohmic resistance. In many chemiresistor designs, the change in ohmic resistance may provide a quantitative basis for measurement of the absorbed species. Chemiresistors may generally be comprised of an electrically insulating substrate, with at least one surface having two or more conductive electrode layers spaced apart thereon. These electrodes may comprise a metallic layer, and they may have an interdigitated geometric form. A chemiresistive layer or "ink" may cover two or more electrode layers, and act as the "absorber" that attracts the analyte species of interest. Voltage applied to the electrodes will induce a current flow within the chemiresistive ink layer. Measurement of this current may provide a quantitative basis for detection of absorbed analyte.

Absorption of a species by a chemiresistive layer results in changes in the layer's physical and/or chemical properties, resulting in a change in ohmic resistance. For example, a chemiresistive ink may comprise finely divided carbon particles in a polymeric binder. The proportion of binder and particles may be chosen such that the layer has a first ohmic resistance. Upon absorption of an organic compound having affinity for the polymeric binder, the layer may undergo swelling which causes the particles to generally move out of contact, resulting in high ohmic resistance. The change in ohmic resistance due to swelling may be in proportion to the organic compound. Heating of the layer may desorb the organic compound, regenerating the layer for a new cycle of measurement.

SUMMARY

Embodiments according to the invention can provide methods, devices, systems, and compositions for monitoring gases. In some embodiments according to the invention, a device can include a visible light emitter circuit that is configured to provide emitted visible light into a breathing circuit. A first visible light sensor circuit can be configured to receive a first portion of the emitted visible light and a second visible light sensor circuit can be configured to receive a second portion of the emitted visible light. A processor circuit can be coupled to the visible light emitter circuit and to the first and second visible light sensor circuits, where the processor circuit can be configured to determine a CO2 level of a respiratory stream in the breathing circuit based on the first and second portions of the emitted visible light.

In some embodiments according to the invention, the first visible light sensor circuit can be configured to provide a reactive signal to the processor circuit as a color indication of the CO2 level based on the first portion of the emitted visible light. In some embodiments according to the invention, the second visible light sensor circuit can be configured to provide a control signal to the processor circuit as a color indication irrespective of the CO2 level based on the second portion of the emitted visible light. In some embodiments according to the invention, the control signal can include an ambient light control component and color control component.

In some embodiments according to the invention, the first visible light sensor circuit can be configured to provide a reactive signal to the processor circuit as a color indication of the CO2 level based on the first portion of the emitted visible light. The second visible light sensor circuit can be configured to provide a control signal to the processor circuit as a color indication irrespective of the CO2 level based on the second portion of the emitted visible light.

In some embodiments according to the invention, a method of monitoring a respiratory stream can be provided by monitoring color change of a color change material to determine a $CO_2$ level of the respiratory stream in contact with the color change material by emitting visible light onto the color change material.

In some embodiments according to the invention, the method can further include sensing the color change using a sensor to detect a portion of the emitted visible light reflected from and/or transmitted through the color change material. As those skilled in the art will recognize, in some embodiments, a portion of the emitted visible light may be reflected from the color change material and a portion of the emitted visible light may be transmitted through the color change material, and a sensor may be configured to detect either portion or both portions. An embodiment describing a sensor detecting a portion of the reflected emitted visible light can be configured to detect a portion of the transmitted emitted visible light. In certain embodiments according to the invention, the method can include using a sensor to detect a portion of the emitted visible light reflected from and/or transmitted through a control material, which may not change color when in contact with $CO_2$. The method may thus include comparing a portion of the emitted visible light reflected from and/or transmitted through the color change material and a portion of the emitted visible light reflected from and/or transmitted through a control material.

In some embodiments according to the invention, the method can further include determining the $CO_2$ level based on a comparison of components of the emitted visible light reflected from and/or transmitted through the color change material and/or control material. In some embodiments according to the invention, the components include at least two color components of the emitted visible light reflected from and/or transmitted through the color change material and/or control material. In some embodiments according to the invention, the at least two color components of the emitted visible light reflected from and/or transmitted through the color change material and/or control material comprise red, green, and blue components.

In some embodiments according to the invention, the determining can be provided by determining the $CO_2$ level based on a comparison of at least two of a red component, a green component, and a blue component of the emitted visible light reflected from and/or transmitted through the color change material and/or control material.

In some embodiments according to the invention, an apparatus to monitor a respiratory stream can include a color change material and/or control material that can be positioned proximate to the respiratory stream and an electronic visible light emitter can be configured to emit visible light onto the color change material and/or control material.

In some embodiments according to the invention, the apparatus can include an electronic visible light sensor, that can be positioned to receive at least a portion of the emitted visible light reflected from and/or transmitted through the color change material and/or control material. An apparatus according to embodiments of the invention may include two or more electronic visible light sensors. In certain embodiments according to the invention the apparatus may comprise at least two electronic visible light sensors, wherein one sensor may be positioned to receive at least a portion of the emitted visible light reflected from and/or transmitted through the color change material and the other sensor may be positioned to receive at least a portion of the emitted visible light reflected from and/or transmitted through the control material.

In some embodiments according to the invention, the electronic visible light emitter and the electronic visible light sensor are remote from the respiratory stream, and the apparatus can further include an optical transmission medium that extends from the color change material and/or control material to the electronic visible light emitter and the electronic visible light sensor, that can be configured to conduct the emitted visible light onto the color change material and/or control material and to conduct the emitted visible light reflected from and/or transmitted through the color change material and/or control material.

In some embodiments according to the invention, the apparatus can further include a breathing circuit adapter having the color change material and/or control material mounted on an interior side wall thereof, wherein a major surface of the color change material and/or control material is parallel to a direction of the respiratory stream in the adapter.

In some embodiments according to the invention, a composition for use in monitoring a respiratory stream, referred to herein as a color change indicator, can be configured to change from a first color to a second color in response to an increase in $CO_2$ within the respiratory stream, where the first color includes more of a first component than a second component or more than a third component and the second color includes less of the first component than the second component or less than the third component. In certain embodiments according to the invention, a color change material, which can include a color change indicator, can be configured to change from a first color to a second color in response to an increase in $CO_2$ within the respiratory stream, where the first color includes more of a first component than a second component or more than a third component and the second color includes less of the first component than the second component or less than the third component. In certain embodiments according to the invention, a control composition for use in monitoring a respiratory stream can include a control material configured to remain a first color in response to an increase and/or decrease in $CO_2$ within the respiratory stream, where the first color includes more of a first component than a second component or more than a third component.

In some embodiments according to the invention, the first component can be blue and the second and third components can be red and green, respectively. In some embodiments according to the invention, the first color includes more of the first component than both the first and second components and the second color includes less of the first component than both the second and third components.

In some embodiments according to the invention, a composition comprising: a dye present in an amount of about 0.001% to about 0.1% by weight of the composition; a buffer present in an amount of about 0.5% to about 10% by weight of the composition; an alkaline material present in an amount of about 0.1% to about 10% by weight of the composition; and a nitrogen containing compound present in an amount of about 0.01% to about 2% by weight of the composition may be provided. The nitrogen containing compound may be configured to provide an increase in a colorific response. According to some embodiments, the composition may be used to determine a $CO_2$ concentration, such as, but not limited to, a $CO_2$ concentration in a respiratory stream.

In some embodiments according to the invention, a color change material may be provided. The color change material may comprise a substrate; and a color change composition according to embodiments described herein, and the color change composition may be in contact with at least a portion of the said substrate. According to some embodiments, the substrate is optically transmissive.

In some embodiments according to the invention, a carbon dioxide indicator may be provided. The carbon dioxide indicator may comprise a color change material, wherein said color change material is responsive to carbon dioxide; and a control material, wherein said control material is substantially non-responsive to carbon dioxide.

In some embodiments according to the invention, a kit may be provided. The kit may comprise a carbon dioxide indicator, wherein at least a portion of said carbon dioxide indicator is responsive to carbon dioxide; a support member, wherein said carbon dioxide indicator is attached to said support member; and a storage bag configured to isolate said carbon dioxide indicator from external carbon dioxide.

In some embodiments according to the invention, a method of determining a carbon dioxide level in a subject's respiratory stream is provided. The method may comprise contacting said respiratory stream to a color change material according to embodiments described herein; and monitoring color change of the color change material by emitting visible light onto the color change material, thereby determining a carbon dioxide level of the respiratory stream in contact with said color change material.

BRIEF DESCRIPTION OF THE DRAWINGS

FIG. 8 is a schematic representation of a $CO_2$ detection system in some embodiments according to the invention.

FIG. 9 is a schematic representation of a $CO_2$ detection system in some embodiments according to the invention.

DESCRIPTION OF EMBODIMENTS ACCORDING TO THE INVENTION

Figure 1:
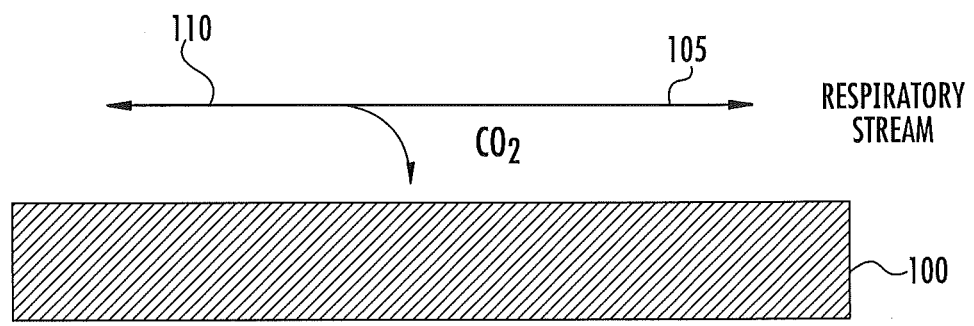
FIG. 1 is a schematic illustration of a color change material configured for placement within a breathing circuit for contact with $CO_2$ in some embodiments according to the invention.

Embodiments of the present inventive subject matter are described hereinafter with reference to the accompanying drawings, in which embodiments of the present inventive subject matter are shown. This present inventive subject matter may, however, be embodied in many different forms and should not be construed as limited to the embodiments set forth herein. Rather, these embodiments are provided so that this disclosure will be thorough and complete, and will fully convey the scope of the present inventive subject matter to those skilled in the art. Like numbers refer to like elements throughout.

It will be understood that in the embodiments discussed herein, the respiratory gasses can be those inhaled/exhaled by any living organism, such as a human, an animal, etc. Accordingly, the respiratory gas is referred to as being inhaled/exhaled by a subject, which can refer to any living organism.

In still further embodiments according to the invention, it will be understood that the use of the systems for the detection of $CO_2$ can be implemented in any environment where the measurement of $CO_2$ may be desirable. For example, in some embodiments according to the invention, systems, etc. for the detection of $CO_2$ as described herein may be implemented as part of mass transit systems (such as trains, airplanes, buses, etc.), places where large crowds congregate, such as stadiums etc., environments where the level of $CO_2$ in a subject undergoing physical exercise may be monitored, such as during running, training, or other physical exertion with a level of $CO_2$ expired by the subject may be relevant. In still other embodiments according to the invention, systems as described herein may be utilized to detect the level of $CO_2$ in closed breathing systems other than those normally associated with medical procedures, such as use with fire fighting breathing apparatus, mining environments, underwater breathing equipment (i.e., scuba), space applications, and military applications, etc.

In other embodiments according to the invention, the level of $CO_2$ associated with a subject may be provided in environments such as emergency situations wherein $CO_2$ levels may be determined by first responders, where such first responders would utilize what is commonly referred to as an emergency $CO_2$ detector in connection with an endotracheal tube. In still other embodiments according to the invention, the level of $CO_2$ described herein may be determined in association with the administration of IV sedation, such as that used during dentistry or other medical procedures where full anesthesia is not required or used.

It will be understood that the levels of $CO_2$ using systems, devices, methods, etc. as described herein can be utilized in any system that employs a breathing circuit. Such environments may include a ventilator, a respirator, etc., which may be used in conjunction with the administration of anesthesia in an operating room, emergency room, etc. where a level of $CO_2$ may provide an accurate and relatively quick indication of heart/lung function and otherwise provide medical professionals with an indication of the patient's stability.

In some embodiments according to the invention, the $CO_2$ detection systems may be utilized in what is referred to as an open breathing environment, where the color change material included in the system is not housed within a tube or other full enclosure through which the respiratory gas stream flows. Other types of environments and applications are also described herein.

Further, it will be understood that although many embodiments are described herein as using visible light from an electronic emitter, other types of light many be used to determine levels of $CO_2$ consistent with the inventive concepts described herein.

As appreciated by the present inventors, various existing $CO_2$ detection schemes may rely on a visual color change in a detector configured with colored paper responsive to $CO_2$ absorption. Such detectors can indicate the presence or absence of $CO_2$ in a respiratory stream, and are commonly used in emergency medical settings. However, these detectors generally do not provide sufficient accuracy to guide clinical decisions regarding effectiveness of emergency procedures such as ventilation and/or CPR. As further appreciated by the present inventors, conventional devices may have limitations which may include lack of quantifiable results, relative insensitivity, time dependent and temperature sensitive decay of reagents, and poor visibility in less than optimal light conditions.

Moreover, such devices may have limitations with respect to working life once activated, since $CO_2$ absorption from the atmosphere or from the respiratory gas stream eventually exhausts the capacity of the absorber in the detector.

Embodiments according to the invention can provide for colorimetric detection of $CO_2$ in a stream of respiratory gases using electronically generated visible light and electronic detection of the colorimetric change. Accordingly, in some embodiments according to the present invention, a color change material can be placed in contact with the respiratory stream, such as when located on the interior wall of a portion of breathing circuit. A control material, according to some embodiments of the present invention, may also be placed in contact with the respiratory stream, such as when located on the interior wall of a portion of breathing circuit, or may be not be in contact with the respiratory stream. A first surface of the color change material and/or control material can be in contact-with the interior wall while a second surface can be in contact with at least a portion of the respiratory stream. In certain embodiments, a color change material (sometimes referred to herein as a reactive portion) and/or control material (sometimes referred to herein as an unreactive portion) may be configured to be removably attached to a portion of a $CO_2$ detection system and/or device. A control material may be a portion of a color change material or may be separate from a color change material. When a control material is a portion of a color change material there optionally may be a delineation or mark to separate and/or indicate the color change material and the control material.

Carbon dioxide gas within the respiratory stream may diffuse partially into the color change material (which includes a composition referred to as a color change indicator), where it may undergo absorption and/or reaction with components within the layer. Absorption and/or reaction within the layer may result in a color change of the indicator within the layer that is indicative of the amount of $CO_2$ absorbed by the layer and thereby may provide an indication of $CO_2$ in the respiratory stream. The color change material may be configured to permit rapid absorption and desorption of $CO_2$ in order to facilitate sensing of a time-varying level of $CO_2$ in the respiratory stream and may be reversible in that variation of the $CO_2$ is indicated as the gas is exhaled/inhaled. Exemplary materials or substrates for the color change material and/or control material include, but are not limited to, a cellulosic material such as paper (e.g., filter paper, ink jet paper, and chromatography paper), woven, and non-woven materials, a clay material, a mineral material, and any combination thereof.

In some embodiments, a substrate for a color change material and/or control material is optically transmissive. "Optically transmissive," as used herein, refers to the ability of a substrate to allow for light in a region of the light spectrum in a range of about 300 nm to about 900 nm, or any range and/or individual value therein such as, for example, light in the visible region of the light spectrum of about 400 nm to about 700 nm, to pass through the substrate. Accordingly, the optically transmissive substrate does not reflect all (100%) light in a range of about 300 nm to about 900 nm. In certain embodiments, an optically transmissive substrate reflects about 98% or less, about 97% or less, about 95% or less, about 90% or less, about 85% or less, about 80% or less, or about 70% or less of light in a range of about 300 nm to about 900 nm or about 400 nm to about 700 nm.

Carbon dioxide gas within the respiratory stream may also diffuse partially into the control material (which may include a control composition). In some embodiments according to the invention, the $CO_2$ may undergo absorption and/or reaction with components within at least one layer of the control material, but the color of the control material in operation remains substantially the same. Thus, the control material may act as a color standard or reference that may be compared with one or more colors of the color change material. In certain embodiments, a control material may be indicative of the shelf life of the system and/or device. For example, a change in the color of the control material may indicate that the system and/or device is no longer suitable for use. In some embodiments, a control material indicates that the system and/or device is no longer suitable for use when the color of control material in operation does not remain substantially the same.

A color change material, system, and/or device according to embodiments of the present invention may have a shelf life of at least about 3 months, 6 months, 9 months, 1 year, 2 years, 3 years, 4 years, 5 years, or more. "Shelf life," as used herein, refers to the length of time the color change material, system, and/or device maintains the ability to respond to $CO_2$ in an unopened package stored under recommended storage conditions, such as, but not limited to, stored at about 15° C. to about 30° C. or about room temperature (i.e., about 20° C.). The shelf life may, for example, be evidenced by a "use by" or "best if used by" date for the color change material, system, and/or device; the manufacturer's expiration date of the color change material, system, and/or device; and/or the actual characteristics of the color change material, system, and/or device after a specified period of time. Accordingly, the term "shelf life" as used herein should be construed as including both an "actual" shelf life of the color change material, system, and/or device and a "predicted" shelf life of the color change material, system, and/or device unless stated otherwise.

A color change material and/or control material may be dry, partially hydrated, or hydrated. The term "dry" as used herein means that the color change material and/or control material has a moisture content of less than about 5% by weight of the color change material and/or control material compared to the moisture content at full hydration as measured after 24 hours in an aqueous solution at ambient conditions. The term "partially hydrated" as used herein means that the color change material and/or control material has a moisture content that is 50% or less by weight of the color change material and/or control material, typically less than about 75% of the color change material and/or control material, compared to the moisture content at full hydration as measured after 24 hours in an aqueous solution at ambient conditions. "Hydrated," as used herein means that the color change material and/or control material has a moisture content that is about 51% or greater by weight of the color change material and/or control material compared to the moisture content at full hydration (i.e., 100% hydrated) as measured after 24 hours in an aqueous solution at ambient conditions.

In some embodiments, a color change material and/or control material may be dry prior to use and/or dry in a kit according to embodiments of the present invention. In other embodiments, a color change material and/or control material may be partially hydrated or hydrated prior to use and/or partially hydrated or hydrated in a kit according to embodiments of the present invention. In operation, the moisture content of the color change material and/or control material may increase. Thus, in some embodiments, a color change material and/or control material that is dry prior to use may become partially hydrated or hydrated in operation upon contact with moisture present in a respiratory stream and/or ambient air.

Respiratory gas flow may be confined within, for example, a tube that makes up part of the breathing circuit. The color change material and/or control material can be located in any portion of the interior of the tube and oriented to allow the respiratory stream to flow across the major surface of the material. Alternatively or in addition, the control material may be configured to be not in contact with the respiratory stream, such as outside the tube interior. An electronic emitter (sometimes referred to as a visible light emitter circuit) can provide a visible light source with suitable color output and may be positioned outside the tube, such that a portion of emitted light is projected through the wall of the tube to illuminate the color change material and/or control material. An electronic sensor (sometimes referred to herein as a visible light sensor circuit) can detect the color change exhibited by the color change material, which can then be used to indicate the level of $CO_2$ in the respiratory stream. Another electronic sensor can detect the color of the control material, which may be compared to the color exhibited by the color change material.

FIG. 1 is a schematic illustration of a color change material 100 that is configured for inclusion within a breathing circuit in some embodiments according to the invention. According to FIG. 1, the color change material 100 is configured for contact with a subject's respiratory stream. The color change material 100 is positioned within the stream so that when the subject exhales, exhaled gas contacts the major surface of the color change material 100 in the first direction 105. When the subject inhales, inhalation gas is drawn across the major surface of the color change material 100 in the direction 110 which is generally opposite to the direction 105.

It will be understood that the generation of the exhalation gas in the direction 105 and the inhalation gas in the direction 110 is generally referred to herein as a cycle of breathing (i.e., cycle) and further that the exhalation 105 and the inhalation 110 are referred to together as a respiratory gas. It will be further understood that portions of the respiratory gas can flow in other directions which are not parallel to the major surface of the color change material 100. It will be further understood that the color change material 100 is positioned within the breathing circuit so that the respiratory gas is drawn across the major surface of the color change material 100 during the breathing cycle in a repeatable and consistent fashion. Accordingly, the orientation of the color change material 100 within the breathing circuit can reduce obstruction to the respiratory gas. For example, such configurations of the color change material 100 within the breathing circuit can be provided when, for example, the color change material 100 is placed "in-line" in an endotracheal tube or near an exit port of a face mask (such as a mask used for the administration of anesthesia), or in-line with a spirometer, etc.

The color change material 100 shown in FIG. 1 can include a color change indicator configured for detection and measurement of the level of carbon dioxide in the respiratory stream using a reversible color change in response to the presence of carbon dioxide. It will be understood that the color change indicator can be a composition that is impregnated or otherwise included in and/or on the color change material 100. In some embodiments, at least a portion of the color change material 100 is contacted with a color change indicator such as by impregnating, immersing, painting, soaking, submerging, dipping, and the like.

In some embodiments according to the invention, the color change indicator can include an alkaline material. An alkaline material present in a color change indicator may be reactive to gaseous carbon dioxide and may thereby change the pH of a portion of the color-change layer in contact with a respiratory stream containing carbon dioxide. Exemplary alkaline materials may include sodium carbonate, potassium carbonate, calcium carbonate, magnesium carbonate, sodium hydroxide, potassium hydroxide, primary, secondary, or tertiary amines, or combinations thereof. In some embodiments according to the invention, an alkaline material is present in the color change indicator in an amount of about 0.1% to about 20% by weight of the composition, or any range and/or individual value therein, such as about 0.1% to about 10% or about 1% to about 5% by weight of the composition. In certain embodiments, an alkaline material is present in the color change indicator in an amount of about 0.1%, 0.25%, 0.5%, 0.75%, 1%, 1.25%, 1.5%, 1.75%, 2%, 3%, 4%, 5%, 6%, 7%, 8%, 9%, 10%, 11%, 12%, 13%, 14%, 15%, 16%, 17%, 18%, 19%, or 20% or any range and/or individual value therein. In some embodiments according to the invention, the color change indicator comprises sodium carbonate in an amount of about 0.5% to about 2% by weight of the composition, and in certain embodiments, in an amount of about 1.25% by weight of the composition.

In some embodiments according to the invention, the color change indicator can include a dye or pigment. A dye or pigment present in a color change indicator may undergo reversible color change in response to change in pH. Exemplary dyes or pigments may include metacresol purple, thymol blue, and phenol red, and combinations thereof. In some embodiments according to the invention, the color change indicator may include two or more dyes or pigments. In some embodiments according to the invention, a dye or pigment is present in the color change indicator in an amount of about 0.001% to about 2% by weight of the composition, or any range and/or individual value therein, such as about 0.001% to about 1% or about 0.01% to about 1% by weight of the composition. In certain embodiments, a dye or pigment is present in the color change indicator in an amount of about 0.001%, 0.0025%, 0.005%, 0.0075%, 0.01%, 0.025%, 0.075%, 0.1%, 0.25%, 0.5%, 0.75%, 1%, 1.25%, 1.5%, 1.75%, or 2%, or any range and/or individual value therein. In some embodiments according to the invention, the color change indicator comprises metacresol purple in an amount of about 0.001% to about 0.05% by weight of the composition, and in certain embodiments, in an amount of about 0.015% by weight of the composition.

In some embodiments according to the invention, the color change indicator can include one or more buffers. One or more buffers present in a color change indicator may modify the pH of the color-change layer and/or aid in maintaining a particular pH or pH range. Buffers may also be selected to provide a faster response time, better reversibility, and longer life. Exemplary buffers include aqueous solutions of sodium bisulfate, sodium carbonate, and mixtures thereof. In some embodiments according to the invention, the color change indicator can be configured to undergo a change in color and/or color saturation in the presence of a metabolically relevant carbon dioxide concentration. In some embodiments according to the invention, a buffer is present in the color change indicator in an amount of about 0.1% to about 20% by weight of the composition, or any range and/or individual value therein, such as about 0.1% to about 10% or about 1% to about 5% by weight of the composition. In certain embodiments, a buffer is present in the color change indicator in an amount of about 0.1%, 0.25%, 0.5%, 0.75%, 1%, 1.25%, 1.5%, 1.75%, 2%, 3%, 4%, 5%, 6%, 7%, 8%, 9%, 10%, 11%, 12%, 13%, 14%, 15%, 16%, 17%, 18%, 19%, or 20% or any range and/or individual value therein. In some embodiments according to the invention, the color change indicator comprises sodium bisulfate in an amount of about 1% to about 5% by weight of the composition, and in certain embodiments, in an amount of about 2% by weight of the composition. In some embodiments according to the invention, the color change indicator comprises an alkaline material, a dye or pigment, and one or more buffers.

In some embodiments according to the invention, the color change indicator can include a water-attractive component. A water-attractive component present in a color change indicator may facilitate hydration of a color-change layer in the presence of vapor-phase moisture in the respiratory stream. Exemplary water-attractive components may include glycerol, propylene glycol and mixtures thereof. In some embodiments according to the invention, a water-attractive component is present in the color change indicator in an amount of about 1% to about 75% by weight of the composition, or any range and/or individual value therein, such as about 5% to about 50% or about 10% to about 30% by weight of the composition. In certain embodiments, a water-attractive component is present in the color change indicator in an amount of about 1%, 5%, 10%, 15%, 20%, 25%, 30%, 35%, 40%, 45%, 50%, 55%, 60%, 65%, 70%, or 75% or any range and/or individual value therein. In some embodiments according to the invention, the color change indicator comprises glycerin in an amount of about 5% to about 45% by weight of the composition, and in certain embodiments, in an amount of about 25% by weight of the composition. In some embodiments according to the invention, the color change indicator comprises an alkaline material, a dye or pigment, one or more buffers, and a water-attractive component.

In some embodiments according to the invention, the color change indicator can include surface modifying additives including ionic and nonionic surfactants. Exemplary surfactants include, but are not limited to, amines, such as mono-, di-, and trimethanolamine, and quaternary ammonium compounds, such as benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride and domiphen bromide. In some embodiments according to the invention, a surface modifying additive is present in the color change indicator in an amount of about 0.1% to about 10% by weight of the composition, or any range and/or individual value therein, such as about 0.1% to about 5% or about 0.1% to about 1% by weight of the composition. In certain embodiments, a surface modifying additive is present in the color change indicator in an amount of about 0.1%, 0.25%, 0.5%, 0.75%, 1%, 1.25%, 1.5%, 1.75%, 2%, 3%, 4%, 5%, 6%, 7%, 8%, 9%, or 10% or any range and/or individual value therein. In some embodiments according to the invention, the color change indicator comprises sodium lauryl sulfate in an amount of about 0.1% to about 1% by weight of the composition, and in certain embodiments, in an amount of about 0.2% by weight of the composition.

In some embodiments according to the invention, the color change indicator can include an antimicrobial additive. An antimicrobial additive present in a color change indicator may inhibit growth of bacteria, molds, funguses or other microbes. Exemplary antimicrobial additives include, but are not limited to, hexachlorophene; cationic biguanides such as chlorhexidine and cyclohexidine; iodine and iodophores such as povidone-iodine; halo-substituted phenolic compounds such as PCMX (i.e., p-chloro-m-xylenol), triclocarban, and triclosan (i.e., 5-chloro-2-(2,4-dichlorophenoxy)phenol); furan medical preparations such as nitrofurantoin and nitrofurazone; methenamine; aldehydes such as glutaraldehyde and formaldehyde; alcohols; metal-containing therapeutics such as silver-containing therapeutics or zinc-containing therapeutics; and any combination thereof. In some embodiments according to the invention, an antimicrobial additive is present in the color change indicator in an amount of about 1 part per million (ppm) to about 1000 ppm, or any range and/or individual value therein, such as about 5 ppm to about 500 ppm or about 10 ppm to about 50 ppm. In certain embodiments, an antimicrobial additive is present in the color change indicator in an amount of about 1, 5, 10, 20, 30, 40, 50, 60, 70, 80, 90, 100, 150, 200, 300, 400, 500, 600, 700, 800, 900, or 1000 ppm or any range and/or individual value therein. In some embodiments according to the invention, the color change indicator comprises triclosan in an amount of about 1 ppm to about 50 ppm, and in certain embodiments, in an amount of about 20 ppm.

According to some embodiments, a color change material and/or color change indicator may be configured to provide an increase in a colorific response. "Colorific response," as used herein, refers to the magnitude of the color change and/or color saturation in the color change material and/or color change indicator when in the presence of a metabolically relevant carbon dioxide concentration and/or the rate at which the color change material and/or color change indicator responds between metabolically relevant carbon dioxide concentrations. In some embodiments, a color change material and/or color change indicator may comprise means for catalyzing an increase in a colorific response, such as, but not limited to, a catalyst configured to provide an increase in a colorific response. Means for catalyzing an increase in a colorific response may increase the magnitude of the color change and/or color saturation in the color change material and/or color change indicator when in the presence of a metabolically relevant carbon dioxide concentration and/or the color change rate between metabolically relevant carbon dioxide concentrations compared to the colorific response in the absence of the means for catalyzing an increase in a colorific response. Thus, means for catalyzing an increase in a colorific response may increase the sensitivity of the color change indicator, color change material, and/or $CO_2$ detection system and/or device when present in a color change material and/or color change indicator. "Color change rate," as used herein, refers to the rate at which the color change material and/or color change indicator changes from a first color to a second color and/or the rate at which the color change material and/or color change indicator changes from the second color to the first color. Thus, the color change rate may refer to the rate at which the color change material and/or color change indicator reversibly changes.

In particular embodiments, means for catalyzing an increase in a colorific response may be present in the color change material and/or color change indicator in an amount sufficient to increase the sensitivity of the color change indicator, color change material, and/or $CO_2$ detection system and/or device. Means for catalyzing an increase in a colorific response may be present in the color change material and/or color change indicator in an amount sufficient to increase the sensitivity of the color change indicator, color change material, and/or $CO_2$ detection system and/or device by at least about 5%, 10%, 20%, 30%, 40%, 50%, 60%, 70%, 80%, 90%, 100%, 125%, 150%, 200%, 300% or more, or any range and/or individual value therein compared to the sensitivity of the color change and/or color saturation in the absence of a means for catalyzing an increase in a colorific response in the color change material and/or color change indicator.

In certain embodiments, the presence of a means for catalyzing an increase in a colorific response in the color change material and/or color change indicator may increase the magnitude of the color change and/or color saturation by a factor of about 1.2 to about 20 or more, or any range and/or individual value therein, compared to the magnitude of the color change and/or color saturation in the absence of a means for catalyzing an increase in a colorific response in the color change material and/or color change indicator. For example, in certain embodiments, the presence of a means for catalyzing an increase in a colorific response in the color change material and/or color change indicator may increase the magnitude of the color change and/or color saturation by a factor of about 1.5, 2, 3, 4, 5, 6, 7, 8, 9, 10, 11, 12, 13, 14, 15, 16, 17, 18, 19, 20, or more, or any range therein, compared to the magnitude of the color change and/or color saturation in the absence of a means for catalyzing an increase in a colorific response in the color change material and/or color change indicator.

According to some embodiments, the presence of a means for catalyzing an increase in a colorific response in a color change material and/or color change indicator may increase the rate at which the color change material and/or color change indicator responds between metabolically relevant carbon dioxide concentrations compared to the rate at which the color change material and/or color change indicator responds between metabolically relevant carbon dioxide concentrations in the absence of a means for catalyzing an increase in a colorific response. Means for catalyzing an increase in a colorific response of the color change material and/or color change indicator may thus increase the color change rate.

A color change material and/or color change indicator may respond to a subject's breathing cycle. In certain embodiments, a color change material and/or color change indicator is configured to provide a color change rate that provides a reversible color change to occur between consecutive breaths. Thus, a color change material and/or color change indicator may be configured to change from a first color to a second color in response to a first metabolically relevant carbon dioxide concentration (e.g., the $CO_2$ concentration in a subject's exhale) and return to the first color before a second metabolically relevant carbon dioxide concentration (e.g., the $CO_2$ concentration in the subject's subsequent exhale) occurs. In particular embodiments, a color change material and/or color change indicator is configured to provide a color change rate that provides for the color change material and/or color change indicator to change from a first color to a second color and return to the first color between about 0 to about 60 times per minute, or any range and/or individual value therein. In certain embodiments, a color change material and/or color change indicator is configured to provide a color change rate that provides for the color change material and/or color change indicator to change from a first color to a second color and return to the first color about 0, 5, 10, 15, 20, 25, 30, 35, 40, 45, 50, 55, 60 or more times per minute, or any range therein.

In certain embodiments, a color change material and/or color change indicator comprises means for catalyzing an increase in a colorific response and the means for catalyzing an increase in a colorific response is configured to increase the color change rate by about 5% or more, such as, but not limited to, about 10%, 20%, 30%, 40%, 50%, 60%, 70%, 80%, 90%, 100%, 150%, 200%, or more or any range and/or individual value therein. In this manner, the means for catalyzing an increase in a colorific response may increase the sensitivity of the color change indicator, color change material, and/or $CO_2$ detection system and/or device when present in a color change material and/or color change indicator.

A color change material and/or color change indicator may be configured to have a desired responsiveness to changes in carbon dioxide concentration. The responsiveness of a color change material and/or color change indicator may be measured by the color change rate. In some embodiments, a color change material and/or color change indicator is configured to have a fast color change rate in reference to a control material and/or control composition, which may be configured to have a slow color change rate or no color change. According to some embodiments, a system and/or device may comprise a first color change material that is configured to have a fast responsiveness to changes in carbon dioxide concentration and a second color change material that is configured to have a slower responsiveness to changes in carbon dioxide compared to the responsiveness of the first color change material. The composition of the color change material and/or color change indicator may provide for differences in the color change rate. In some embodiments, a nitrogen containing compound is configured to provide the desired responsiveness to changes in carbon dioxide concentration. In some embodiments, by increasing the concentration of a nitrogen containing compound in the color change material and/or color change indicator the color change rate may be increased.

As appreciated by the present inventors, in some embodiments, a nitrogen containing compound is configured to provide an increase in a colorific response. A nitrogen containing compound may be a catalyst. In some embodiments, a nitrogen containing compound may be present in an amount sufficient to provide an increase in a colorific response and/or configured to provide an increase in a colorific response. The nitrogen containing compound may comprise an amine and/or ammonium moiety. Exemplary nitrogen containing compounds include, but are not limited to, an amine, a quaternary ammonium compound, an amino acid, an amino acid derivative, and any combination thereof "Amino acid derivative," as used herein, refers to an amino acid substituted with one or more substituents. Exemplary substituents include, but are not limited to, alkyl, lower alkyl, halo, haloalkyl, alkenyl, alkynyl, cycloalkyl, cycloalkylalkyl, heterocyclo, heterocycloalkyl, aryl, arylalkyl, lower alkoxy, thioalkyl, hydroxyl, thio, mercapto, amino, imino, halo, cyano, nitro, nitroso, azido, carboxy, sulfide, sulfone, sulfoxy, phosphoryl, silyl, silylalkyl, silyloxy, boronyl, and modified lower alkyl. Further exemplary nitrogen containing compounds include, but are not limited to, an amine, such as mono-, di-, and trimethanolamine; a quaternary ammonium compound, such as benzalkonium chloride, benzethonium chloride, n-alkyl-n-(2-aminoethyl) piperidine, methylbenzethonium chloride, cetalkonium chloride, cetylpyridinium chloride, cetrimonium, cetrimide, dofanium chloride, tetraethylammonium bromide, didecyldimethylammonium chloride, and domiphen bromide; an amino acid, such as lysine, histidine, arginine, aspartic acid, serine, asparagine, glutamine, cysteine, glycine, alanine, leucine, tryptophan, and proline; an amino acid derivative, such as alanine methyl ester, nitroarginine, acetyllysine, and acetylphenylalanine; and any combination thereof. In some embodiments, means for catalyzing an increase in a colorific response comprises an amine, a quaternary ammonium compound, an amino acid, an amino acid derivative, and any combination thereof. In some embodiments, a color change material and/or color change indicator may comprise monoethanolamine.

In some embodiments according to the invention, means for catalyzing an increase in a colorific response is present in the color change material and/or color change indicator in an amount of about 0.01% to about 5% by weight of the composition, or any range and/or individual value therein, such as about 0.1% to about 3% or about 0.1% to about 1% by weight of the composition. In certain embodiments, means for catalyzing a colorific response is present in the color change material and/or color change indicator in an amount of about 0.01%, 0.025%, 0.05%, 0.075%, 0.1%, 0.25%, 0.5%, 0.75%, 1%, 1.25%, 1.5%, 1.75%, 2%, 2.5%, 3%, 3.5, 4%, 4.5%, or 5%, or any range and/or individual value therein. In some embodiments according to the invention, the color change material and/or color change indicator comprises triethanolamine in an amount of about 0.01% to about 1.5% by weight of the composition, and in certain embodiments, in an amount of about 0.2% by weight of the composition.

Figure 2:
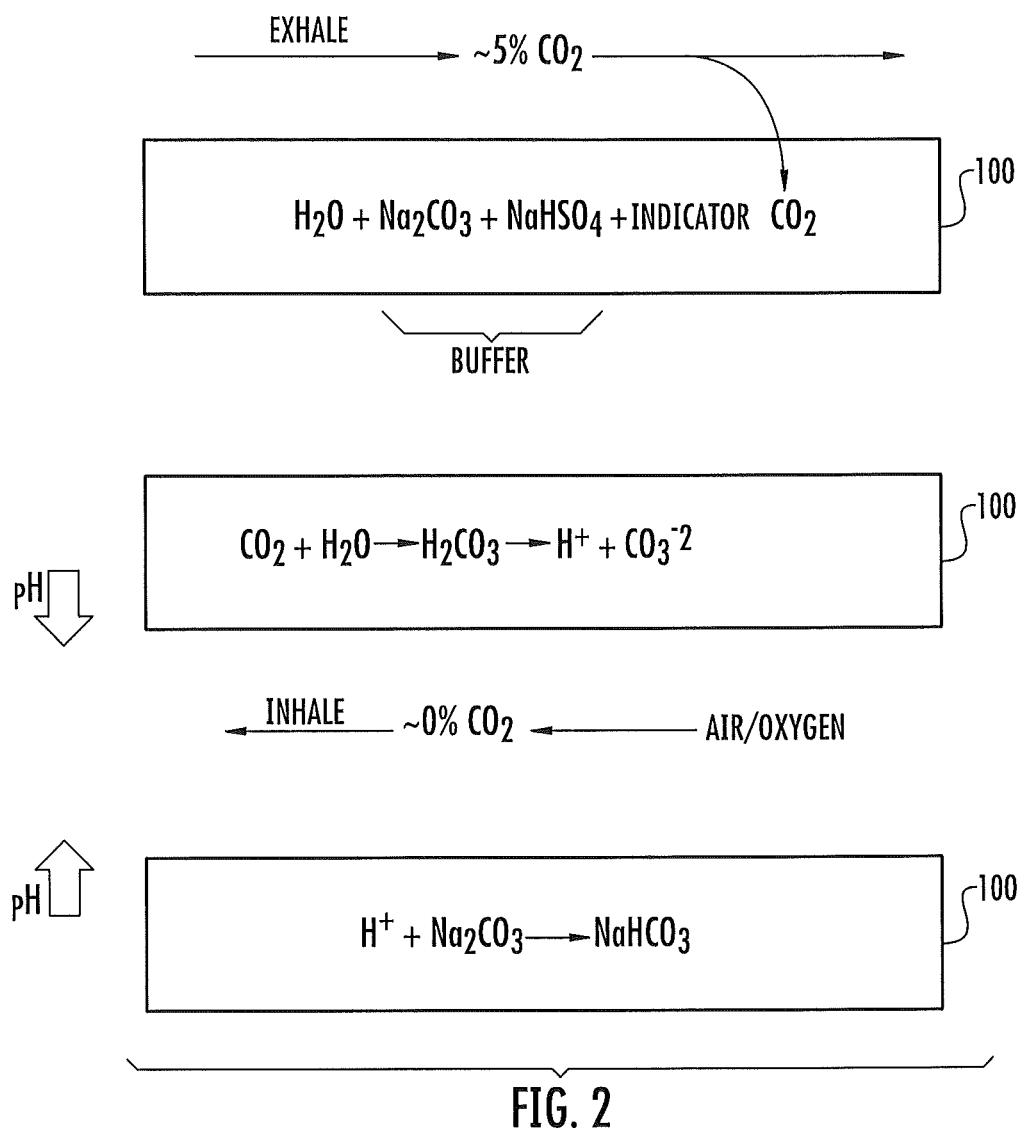
FIG. 2 is a schematic representation illustrating a chemical reaction between a color change indicator included in the color change material and $CO_2$ in contact therewith as part of the breathing cycle in some embodiments according to the invention.

FIG. 2 is a schematic representation of operation of the color change indicator in the color change material 100 responsive to respiratory gas during a breathing cycle in some embodiments according to the invention. According to FIG. 2, respiratory gas including about 5% $CO_2$ contacts the color change material 100. It will be understood that in some embodiments according to the invention, the color change material 100 includes a buffer as well as the color change indicator described herein. According to FIG. 2, the buffer can include $Na_2CO_3$ and $NaHSO_4$ together which operate to stabilize the pH of the color change material 100. Water ($H_2O$) can also be introduced into the color change material 100 via moisture carrier in the respiratory gas during the exhalation portion of the cycle. It will be understood that the pH exhibited by the color change indicator in an initial condition (i.e., prior to the exhalation cycle and the absorption of $CO_2$) can be at a pH from about 7 to about 14, or any range therein, such as, from about 7 to about 12, or from about 8 to about 10. In some embodiments according to the invention, the color change indicator can be at a pH of about 9 or about 8.7.

During the exhale cycle, a portion of the $CO_2$ is absorbed into the color change material 100, whereupon the carbon dioxide and water react to create $H_2CO_3$ whereupon a hydrogen ion (H+) becomes disassociated therewith and also generates the byproducts shown. Because the $CO_2$ is in a gaseous form, the carbon dioxide can diffuse into the color change material 100 faster than the buffer may be able to stabilize the pH so that the hydrogen ions lower the pH of the color change material 100, such that the color exhibited by the color change indicator shifts.

As shown in FIG. 2, during the inhale portion of the breathing cycle, time elapses where no $CO_2$ is introduced into the color change material 100 so the time is provided for the hydrogen ions to combine with the base portion of the buffer to again raise the pH of the color change material 100 to the static condition (e.g., about a pH of 9). It will be understood that the above described breathing cycle is then repeated as the subject continues to breathe. It will be further understood that the amount of the buffer introduced into the color change material 100 can be configured to allow the color change material 100 to exhibit the color change for the desired period of time whereupon the buffer may be replenished for further operation.

According to some embodiments of the invention, a control material may be dyed and/or printed a particular color. A control material may comprise a control composition that may comprise one or more of the same and/or different components as the color change indicator and/or color change material. In certain embodiments, a control composition and/or control material comprises the same dye and optionally one or more of the same buffers as the color change indicator and/or color change material. In particular embodiments, a control composition and/or control material may be configured to provide the control material with a color that is substantially the same color as the color of the color change material in the absence of $CO_2$. Thus, in operation, at the initial time point prior to exposure to a change in $CO_2$ concentration, the control material and color change material may be substantially the same color. Two colors that are substantially the same color have a hue and a value that are substantially the same.

In some embodiments according to the invention, a control composition and/or control material may be configured so that in operation, the control material is not responsive to a change in $CO_2$ concentration, such as, for example, respiratory gas during a breathing cycle. A control composition and/or control material may not be responsive to a change in $CO_2$ concentration by not changing to a color having a hue and value that indicate a change in $CO_2$ concentration. For example, a dye or pigment in the control material and/or control composition may be quenched and/or the pH of the control composition and/or control material may be configured to prevent or minimize a color change and/or a component, such as an alkaline material, may be added in excess to prevent or minimize a color change. Alternatively or in addition, a control material may be configured to be non-responsive to a change in $CO_2$, such as respiratory gas during a breathing cycle, by coating the control material with a coating such as, but not limited to a wax, a film such as a polymeric film, a plastic, and the like. In some embodiments, the coating may be substantially impermeable to vapor and/or respiratory gases.

A control composition and/or control material may be configured to indicate the shelf life of the system and/or device and may according to some embodiments change color after a prolonged period of time, such as for example after about 3 or more months, such as after about 3 months, 6 months, 9 months, 1 year, 2 years, 3 years or more. Thus, the control composition and/or control material may be configured to be responsive to $CO_2$, such as after a particular period of time, and may indicate that the shelf life of the system and/or device has expired.

A control material may be a material that is separate from the color change material. Alternatively or in addition, a control material may be part of the color change material and may optionally be partitioned from the color change material with means for separating the two, such as with a barrier material (e.g., a wax or plastic). In some embodiments, a control material and a color change material may be in close proximity to one another in a device and/or system and/or in a configuration such that the control material and color change material are exposed to substantially the same conditions (e.g., light gas, humidity, etc.). The signal to noise ratio may be used to determine if the control material and the color change material are exposed to substantially the same conditions. In some embodiments, a color change larger than the signal to noise ratio may indicate that the conditions are not substantially the same. In certain embodiments, a color change that is 10% or more above the signal to noise ratio may indicate that the conditions are not substantially the same.

FIGS. 3-6 are schematic illustrations of different configurations of a color change material 100 allowing for different applications in some embodiments according to the invention. In particular, in some configurations the color change material can include a thin material, such as paper, having the color change indicator infused therein. In other embodiments, a separate substrate may be provided to which the color change material is attached. In still other embodiments, the color change material can be supported by what is referred to a mineral support, which can allow the color change indicator to be applied in the form of a composition onto to a surface of the breathing circuit in some embodiments according to the invention.

In some embodiments according to the invention, the color change material 100 can be provided in the form of a unitary format, such as a liquid including color change indicator (which may be, for example sprayed or painted onto a surface) or the color change indicator impregnated into a substrate such as a thin paper. Accordingly, in these embodiments according to the invention, the color change material 100 can be painted or coated onto an interior surface of the breathing circuit. Accordingly, the color change material 100 can include unitary layer with high specific surface area. The unitary layer may be impregnated with chemical species that bring about a reversible color change in response to carbon dioxide in the respiratory stream. The unitary layer may be porous or microporous. Exemplary unitary layers include cellulosic paper, microporous olefinic synthetic paper, and various coatings based on particulates such as clay and/or silica and/or ground limestone and/or purlite and/or talc or other mineral-based materials. Other coatings may contain finely divided cellulose and/or other finely divided organic materials or combinations thereof.

In some embodiments according to the invention, the color change material 100 is a multilayer construction comprising a substrate, a bonding layer, and a color-change layer (including the color change indicator). See, for example, FIGS. 4-6. The substrate may be selected from a variety of thin, rigid or flexible materials such as paper, glass, or plastic films or sheets, or molded plastic articles. Substrate materials may be—optically transparent, reflective, or opaque, or some combination thereof. The substrate material may be selected in order to provide mechanical support for a color-change layer, and also may be selected to have desirable optical properties such as transmission, reflectance, or opacity, to facilitate photometric measurement of the color-change layer. A bonding layer may be applied to the substrate to adhesively attach the color-change layer. The bonding layer may be selected for good mechanical bonding between the color-change layer and the substrate. The bonding layer may further be selected to provide a source of chemical agents that facilitate the color-change chemistry by migration of said agents from the bonding layer into the color-change layer. A color-change layer may be included that has a high specific surface area to facilitate interaction with a respiratory stream. The color change layer may be porous or microporous. The color-change layer may be impregnated with chemical species that bring about a reversible color change in response to carbon dioxide or other exhaled gases in the respiratory stream.

Figure 5:
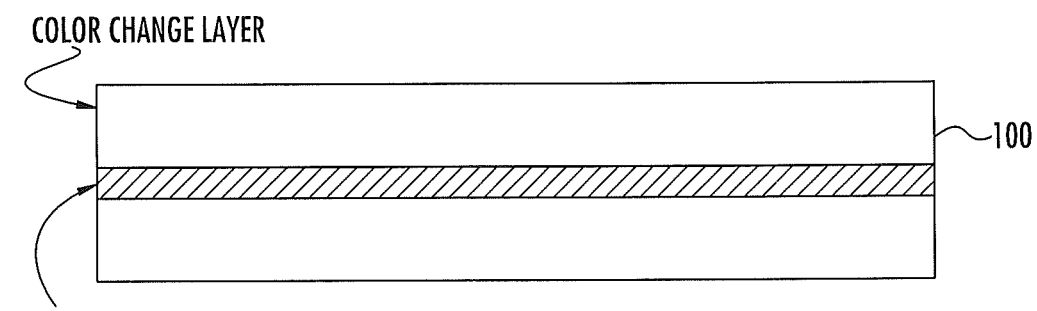

In some embodiments according to the invention, the color change material 100 can be provided as shown for example in FIG. 5, wherein the color change material 100 is a multilayer construction comprising a substrate, a bonding layer, and a color-change layer (including the color change indicator). In this embodiment, the substrate may be a portion of the airway circuit containing at least a portion of a respiratory stream. A bonding layer may be applied to the substrate to adhesively attach the color-change layer. The bonding layer may be selected for good mechanical bonding between the color-change layer and the substrate. The bonding layer may further be selected to provide a source of chemical agents that facilitate the color-change chemistry by migration of said agents from the bonding layer into the color-change layer. A color-change layer may be included that has a high specific surface area to facilitate interaction with a respiratory stream. The color change layer may be porous or microporous. The color-change layer may be impregnated with chemical species that bring about a reversible color change in response to carbon dioxide in the respiratory stream.

Figure 6:
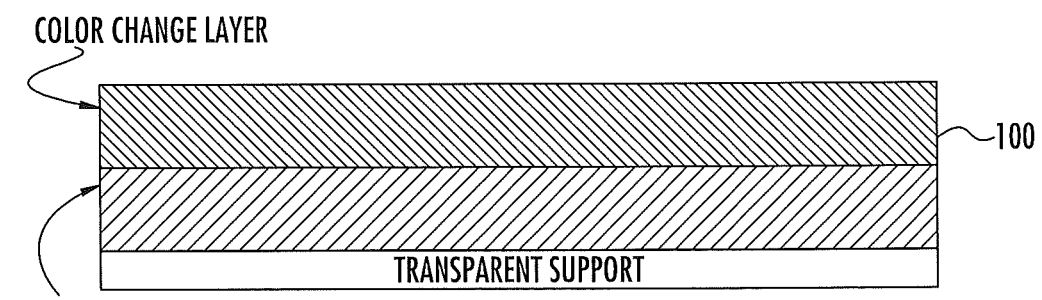

In some embodiments according to the invention, as shown for example in FIG. 6, the color change material 100 is a substantially transparent article, such as a planar waveguide, with a color-change layer adhesively attached to at least one edge of the waveguide, and wherein the portion of the waveguide having a color-layer attached thereto is projected into a portion of a respiratory stream.

Figure 4:
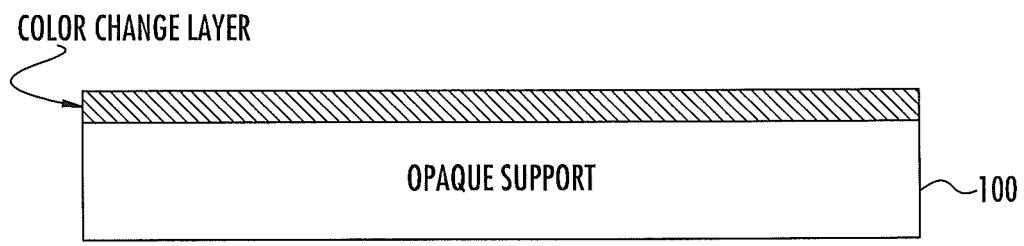

As described herein, the color change material 100 can include a color change indicator, which may be incorporated into the color change material 100 structures shown in FIGS. 4-6, for example, as a color change layer. The color change indicator can provide for the colorimetric response in the presence of $CO_2$. The following examples describe exemplary color change indicators that were fabricated:

Example 1

A color change indicator according to the present invention was fabricated using 0.4 grams of anhydrous sodium bisulfate dissolved in 9.6 grams of water. 5.0 grams of glycerin was added and mixed to dissolve. 1.0 gram of a 0.1% w/w aqueous solution of metacresol purple dye was added and stirred to mix, resulting in a red colored solution. A 10% w/w aqueous solution of anhydrous sodium carbonate was added drop-wise until the color of the solution permanently changed to purple, occurring at a pH of approximately 9.0.

Example 2

Another color change indicator according to the present invention was fabricated using 0.5 grams of anhydrous sodium bisulfate were dissolved in 9.5 grams of water. 5.0 grams of glycerin was added and mixed to dissolve. 1.0 gram of a 0.1% w/w aqueous solution of metacresol purple dye was added and stirred to mix, resulting in a red colored solution. A 10% w/w aqueous solution of anhydrous sodium carbonate was added drop-wise until the color of the solution permanently changed to purple, occurring at a pH of approximately 9.0.

Example 3

A mineral support embodiment as an alternative to the impregnation of paper with the color change indicator was fabricated using 4.0 grams of kaolin clay combined with 2.0 grams of diatomaceous earth (Celite 535), 3.0 grams water, and 1.0 gram of Neocryl A-614 acrylic latex resin (DSM Neoresins) to form a stiff paste. A layer approximately 3 mils in thickness was doctor-bladed onto a heavy poster-paper support and baked in an oven for 5 minutes at 150° C. The resulting layer was nearly white in color, adherent, and had a matte finish.

Example 4

A mineral support was fabricated using 1.0 grams of kaolin clay combined with 5.0 grams of calcium carbonate, 3.0 grams of water, and 1.0 gram of Neocryl A-614 acrylic latex resin (DSM Neoresins) to form a stiff paste. A layer approximately 3 mils in thickness was doctor-bladed onto a heavy poster-paper support and baked in an oven for 5 minutes at 150° C. The resulting layer was nearly white in color, opaque, adherent, with a matte finish.

Example 5

An embodiment of the color change material 100 shown in FIG. 6 was fabricated using a sheet of polycarbonate plastic approximately 30 mils in thickness laminated to a sheet of white paper having a basis weight of approximately 270 g/square meter using an adhesive layer consisting of 3.0 grams of a 10% (w/w) solution of monoethanolamine in methanol and 5.0 grams of Neocryl A-614 acrylic latex resin (DSM Neoresins). The laminated construction was baked in an oven at 100° C. for 5 minutes. The resulting construction had an adherent white paper layer firmly attached to a transparent polycarbonate support layer.

Example 6

Figure 3:
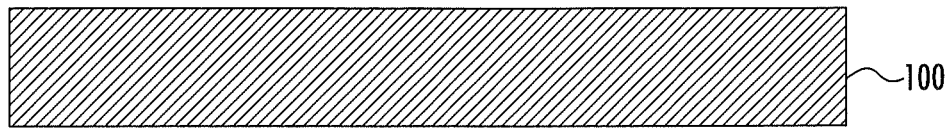
FIGS. 3-6 are schematic representations illustrating different configurations of color change materials in some embodiments according to the invention.

A change color material 100 shown in the embodiment illustrated in FIG. 3 was fabricated using strips of conventional ink jet printer paper approximately 1 inch wide and 2 inches long were soaked in the color change of examples 1 or 2 indicator for 5-10 seconds, drained on absorbent toweling, and baked at about 100° C. for 60 sec. The resulting paper strips had an intense purple color on both sides, were dry to the touch, and spontaneously and reversibly changed in color shade when exposed to physiologically relevant levels of carbon dioxide, e.g. 1-10% (v/v) in air at approximately one atmosphere pressure. Color shade variation in response to carbon dioxide was discernible from either side of the strip.

Example 7

A color change material 100 according to the embodiment illustrated in FIG. 3 was fabricated using strips of mineral support of examples 3 and 4 approximately 1 inch wide and 2 inches long were soaked for 5-10 seconds in Color Change Indicator 2, and baked in an oven at 100° C. for 60 sec. The resulting strips were opaque, had an intense purple color on the mineral-coated side, were dry to the touch, and spontaneously and reversibly changed in color shade when exposed to physiologically relevant levels of carbon dioxide, e.g. 1-10% v/v in air at approximately one atmosphere pressure.

Example 8

A color change material 100 illustrated in FIG. 6 are fabricated using strips of the plastic support of example 5 1 approximately 1 inch wide and 2 inches long were soaked for 5-10 seconds in color change Indicator of examples 1 or 2, and baked in an oven at 100° C. for 60 sec. The resulting strips had an intense purple color, were partially transparent, were dry to the touch, and spontaneously and reversibly changed in color shade when exposed to physiologically relevant levels of carbon dioxide, e.g. 1-10% v/v in air at approximately one atmosphere pressure. The color shade variation was discernible from either side of the plastic support.

Example 9

A color change indicator according to embodiments of the present invention was prepared by dissolving 0.44 gram of anhydrous sodium bisulfate in 9.0 grams of water, adding 5.0 grams of glycerol, stirring to mix, then adding 1.0 gram of an aqueous 0.1% (w/w) solution of metacresol purple. The solution was titrated to a permanent grape-purple color with approximately 1.67 grams of an aqueous 20% (w/w) solution of sodium carbonate monohydrate. Twenty parts by volume of the resulting solution were combined with 2 parts by volume of a solution of benzalkonium chloride (Andwin Scientific part number 190009) and 3 parts by volume of a 10% (w/w) solution of monoethanolamine in methyl alcohol. The resulting solution was brushed onto strips of white paper having a basis weight of approximately 320 grams per square meter, then baked in an oven for 60 seconds at approximately 100 degrees C. The resulting strips had a uniform sky-blue color, were dry to the touch, and spontaneously and reversibly changed in color shade when exposed to physiologically relevant levels of carbon dioxide, e.g. 1-10% v/v in air at approximately one atmosphere pressure. The color shade variation was discernible from either side of the strip.

Example 10

A color change indicator according to embodiments of the present invention was prepared by combining 31.8 g of water, 93.6 g of a 5% of sodium bisulfate solution, 58.2 g of glycerin, 3.6 g of a 1% solution of metacresol purple, 4.8 g of a 10% solution of methanolamine, and 12.6 g of a solution comprising 10% by weight sodium lauryl sulfate and 0.4% by weight triclosan. Then, the composition was titrated with a 10% solution of sodium carbonate to a final pH of 8.7.

According to some embodiments of the present invention, an apparatus for use in monitoring a respiratory stream may be provided. The apparatus may comprise a color change material and at least one part of the color change material may comprise a reactive portion. At least one part of the reactive portion may be configured to be in contact with a respiratory stream. At least one part of the reactive portion is configured to provide a first color based on exposure to a first $CO_2$ level and is configured to change from the first color through a first range of colors to a second color based on exposure to a second $CO_2$ level that is greater than the first $CO_2$ level. In some embodiments, the reactive portion comprises a color change indicator.

The apparatus may also comprise an unreactive portion. The unreactive portion may be spaced apart from the reactive portion of the color change material. In some embodiments, the unreactive portion is separate from the reactive portion. In other embodiments, the unreactive portion comprises at least one part of the color change material. At least one part of the unreactive portion is configured to provide a first color based on exposure to the first $CO_2$ level and is configured to change from the first color through a second range of colors that is smaller than the first range of colors to a third color based on exposure to the second $CO_2$ level. The third color may comprise a hue and value that may not be indicative of a $CO_2$ level. The first color of the reactive portion and the first color of the unreactive portion may be substantially the same color. In some embodiments, if the first color of the reactive portion and unreactive portion are not substantially the same color prior to exposure to the second $CO_2$ level, then the apparatus may be expired and/or past the recommended shelf life. Alternatively or in addition, if the third color of the unreactive portion comprises a hue and value that is indicative of a $CO_2$ level, then the apparatus may be expired and/or past the recommended shelf life.

In some embodiments, the reactive portion and unreactive portion may each comprise a color change indicator comprising a dye and/or an alkaline material. The amount of the alkaline material in the unreactive portion may be configured to provide the unreactive portion with a greater pH than the reactive portion. The higher pH of the unreactive portion may cause a dye present in the unreactive portion to be quenched and/or may cause the color change indicator to be non-responsive to changes in $CO_2$ concentration, while the lower pH of the reactive portion may allow for a dye to be active, such as by absorbing a different wavelength of light, and/or may cause the color change indicator to be responsive to changes in $CO_2$ concentration. In other embodiments, the unreactive portion is free of the color change indicator.

In further embodiments, a carbon dioxide indicator may be provided. A carbon dioxide indicator may comprise a color change material as described herein and a control material as described herein. The color change material may be responsive to carbon dioxide and the control material may be substantially non-responsive to carbon dioxide. The color change material and control material of a carbon dioxide indicator may-be configured to be exposed to substantially the same conditions. In some embodiments, the color change material and the control material are in close proximity to one another and/or are in the same orientation in relation to a respiratory stream.

A color change material may be responsive to carbon dioxide by changing color in response to changes in the concentration of carbon dioxide. Thus, a control material may be substantially non-responsive to carbon dioxide by not changing color in response to changes in the concentration of carbon dioxide and/or by not changing to a color that is indicative of a change in $CO_2$ concentration. In some embodiments, the control material comprises a dye and is configured to be non-responsive to carbon dioxide by quenching the dye. In other embodiments, a control material is printed to have a color that is substantially the same value and hue as the color of the color change material.

The color change material and control material may be substantially the same color at a first $CO_2$ concentration prior to contact with a second $CO_2$ concentration having a greater $CO_2$ concentration. When the carbon dioxide indicator is in operation, this may allow for the color of the color change material to be compared to the color of the control material and may aid in determining the value and/or extent of the change in $CO_2$ concentration. The color change material may be configured to change from a first color to a second color and return to said first color in response to contact with at least one carbon dioxide concentration. In some embodiments, the color change material is configured to change from a first color to a second color and return to said first color about 1 to about 60 times per minute in response to contact with at least two consecutive carbon dioxide concentrations. Thus, the color of the color change material may be reversible in response to a change in $CO_2$ concentration and may reversibly change color at a rate that is responsive to a breathing cycle of a subject. For example, after a first exhale in a breathing cycle, the color change material may return to the first color prior to exposure to an immediately subsequent second exhale in the breathing cycle.

According to some embodiments a kit may be provided. A kit of the present invention may comprise a color change material as described herein or a carbon dioxide indicator as described herein, a support member, and a storage bag. The color change material or carbon dioxide indicator may be attached to the support member. In some embodiments, the color change material or carbon dioxide indicator may be removably attached to the support member. The kit may also comprise a control material as described herein that may optionally be attached, such as removably attached, to the support member. In certain embodiments, the support member comprises a breathing circuit adapter.

The storage bag may be configured to isolate the color change material or carbon dioxide indicator from external carbon dioxide and may be substantially impermeable to carbon dioxide. The storage bag may comprise a polymer such as thermoplastic polymers (e.g., metallic polyethylene terephthalate (METPET)); a metallic foil such as aluminum foil, tin foil, and/or nickel foil; a metal film such as aluminum-evaporated film and/or tin-evaporated film; and any combination thereof. In some embodiments, the storage bag is substantially impermeable to moisture and/or water vapor. The kit may comprise a moisture desiccant, oxygen scavenger (e.g., metal oxygen scavengers), carbon dioxide scavengers, and any combination thereof. Exemplary moisture desiccants include, but are not limited to, silica gel, molecular sieves, calcium chloride, and the like. The kit may comprise a sachet having at least one of a moisture desiccant, oxygen scavenger, and carbon dioxide scavenger. Exemplary carbon dioxide scavengers include, but are not limited to, a metal oxide (e.g., calcium oxide), a metal hydroxide (e.g., calcium hydroxide), silica gel, and any combination thereof. In some embodiments, storage of a color change material or a carbon dioxide indicator in a storage bag, optionally with at least one of a moisture desiccant, oxygen scavenger, and carbon dioxide scavenger, may increase the shelf life of the kit. In certain embodiments, the kit may have a shelf life of at least about 1 year, 2 years, 3 years, or more.

Figure 7B:
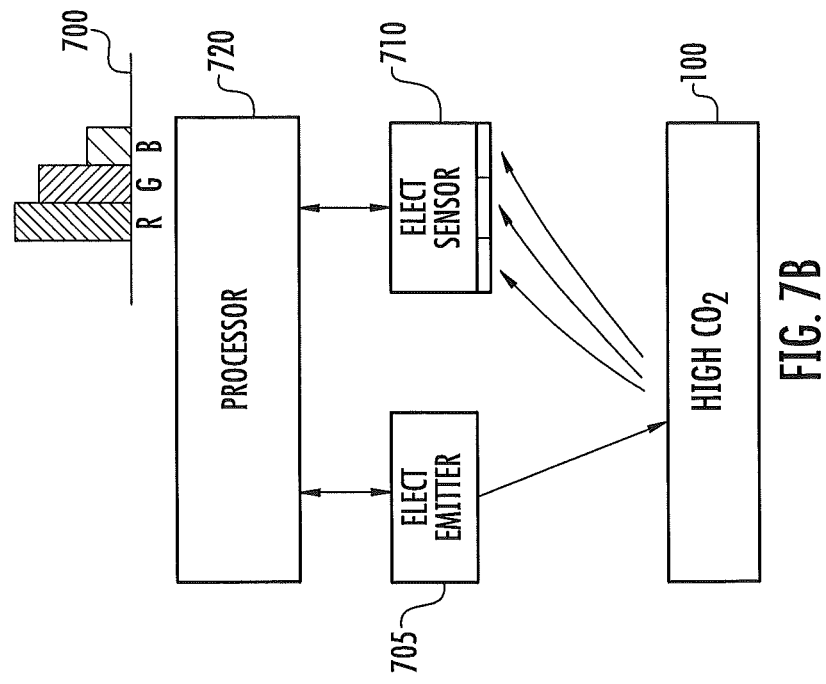
FIG. 7B is a schematic representation of a color change material included in a breathing circuit and exposed to electronically generated visible light and electronic sensing thereof in some embodiments according to the invention.
Figure 7A:
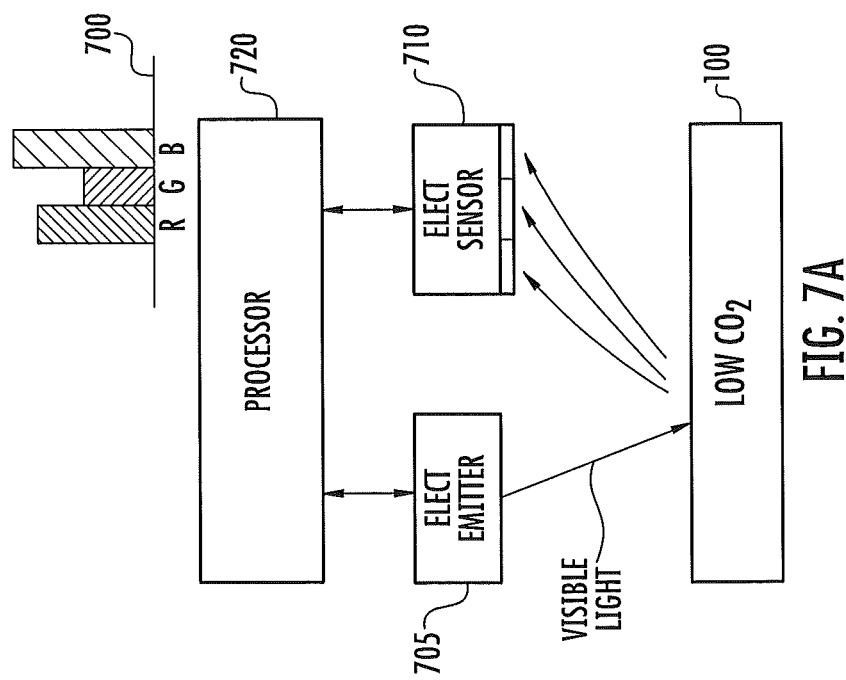
FIG. 7A is a schematic representation of a color change material included in a breathing circuit and exposed to electronically generated visible light and electronic sensing thereof in some embodiments according to the invention.

FIGS. 7A and 7B are schematic illustrations of a $CO_2$ detection system in some embodiments according to the invention. In particular, FIG. 7A illustrates operation of the $CO_2$ detection system 700 where the color change material 100 is exposed to a relatively low concentration of $CO_2$, such as when a subject inhales as part of the breathing cycle. The electronic light emitter 705 emits visible light to illuminate the color change material 100 which is detected by an electronic light sensor 710, both of which can operate under the control of a processor 720. In some embodiments according to the invention, visible light includes light that falls within a range of wavelengths of about 400 nm to about 700 nm, so that at least some of this range may not be perceptible to a human observer without the assistance of embodiments according to the invention.

As described herein, during the inhale portion of the breathing cycle, the relatively low concentration of $CO_2$ in the respiratory stream causes little or no change in the pH of the color change indicator 100 and pH remains generally constant at approximately pH 9. No color shift occurs in the indicator 100 and the reflected light detected by the electronic sensor 710 has a particular value similar in magnitude to the initial color of the color indicator. For example, in some embodiments according to the invention, the value of the reflected light detected by the electronic sensor 710 can be separated into its color components, such as red, green and blue components of the visible light, each of which may be characterized by a particular value, such as an intensity, color value, color temperature etc. In other embodiments according to the invention, the components of the visible light may represent a single color temperature value, which can be represented using, for example, the 1931 CIE chart shown in FIG. 19. The value of the light reflected from the color change indicator 100 and detected by the electronic sensor 710 can indicate the level of $CO_2$ that contacts the color change indicator 100, which can be determined by the processor 720.

FIG. 7B illustrates the same $CO_2$ detector system 700 operating during the exhale portion of the breathing cycle. According to FIG. 7B, the electronic emitter 705 emits visible light to illuminate the color change indicator 100 that is exposed to a relatively high concentration of $CO_2$ during the exhale portion of the breathing cycle. Accordingly, the increased concentration of $CO_2$ in contact with the color change indicator 100 can cause the pH of the color change indicator 100 to decrease (therefore becoming more acidic) which may, in turn, be reflected by a change in color of the color change indicator 100. This change in color can be detected by the electronic sensor 710 which can be represented using the same approach described above in reference to FIG. 7A. Therefore, as the breathing cycle proceeds, the change in the pH of the color change indicator 100 (due to the varying levels of $CO_2$ exposed thereto) can be determined by the electronic sensor 710 analyzing the values of the reflected light.

In some embodiments according to the invention, "white" light can be used as the visible light, which includes components of red, green, and blue. Further, a ratio of the red component to the blue component (in the reflected light) may yield a first value of red-to-blue ratio when the color change indicator 100 is exposed to a relatively low concentration of $CO_2$. As further shown in FIG. 7A, the ratio of the green component to the blue component may also yield an initial first value of green-to-blue ratio in the same situation. It will be further understood that other types of visible light and components thereof may also be utilized.

In contrast, as shown in FIG. 7B, when the color change indicator 100 is exposed to the relatively high concentration of $CO_2$, the ratio of the red component to the blue component may yield a second value that is greater than the first value. As further shown in FIG. 7B, a ratio of the green component to the blue component is also greater than the first value. As appreciated by the present inventors, in some embodiments according to the invention, the green to blue ratio may be less susceptible to noise and to other external factors which can provide a more stable indication of color values detected in the environments illustrated by FIGS. 7A and 7B.

According to FIGS. 7A and 7B, the ratio of one component to another can increase in presence of increased levels of CO2. For example, in FIG. 7A, a relatively low level of CO2 can be evidenced by red, green, and blue color components 80, 50, and 70, respectively. When, however, the level of CO2 increases, as illustrated in FIG. 7B, the color component values can change to, for example, 83, 55, and 71, respectively (where the component values are expressed as values/100). Therefore, a change in the ratio of selected components to one another can indicate the change in CO2.

In some embodiments according to the present invention, a comparison between multiple component values can provide the indication of CO2 levels. In some embodiments according to the invention, a change in a single component value can indicate a change in the CO2 level.

In some embodiments according to the invention, the color change material can be analyzed by selecting a first color or group of colors that become more saturated in the presence of CO2, a second color or group of colors that become less saturated in the presence of CO2, and a third color or group of colors whose saturation is insensitive to the presence of CO2. A scaling factor can be determined for each of the first, second, and third colors and a computational method can be applied to combine the first, second, and third colors and/or their respective scaling factors in order to compute a value representative of the CO2 concentration in the colorimetric sensor, such that the CO2 concentration thereby calculated is relatively insensitive to interference effects from moisture, condensation, or long-term color drift caused by depletion of buffer in the colorimetric sensor material.

In some embodiments according to the invention, the first color or group of colors may be selected to coincide with one or more absorption maxima in the absorption spectra of the at least partially deprotonated indicator dye. In some embodiments according to the invention, the second color or group of colors may be selected to coincide with one or more absorption minima in the absorption spectra of the at least partially protonated indicator dye.

In some embodiments according to the invention, the third color or group of colors may be selected to coincide with one or more isobestic points in the absorption spectrum of the color indicating dye. In some embodiments according to the—invention, the first and second colors or groups of colors may be selected on the basis of computing a maximum signal level in the detector response, regardless of where the colors may fall in the absorption spectrum. In some embodiments according to the invention, an instant ratio of color saturation of colors from the first and second color groups is compared with a time-weighted and/or running average of the color saturation of the first and second color groups. The electronic emitter 705 can be a light emitting device, such as a light emitting diode, along with other support electronics used to operate the LED using the processor 720, such as a driver circuit to provide biasing and current to the LED(s).

A representative example of a white LED lamp includes a package of a blue light emitting diode chip, made of gallium nitride (GaN), coated with a phosphor such as YAG In such an LED lamp, the blue light emitting diode chip produces a blue emission and the phosphor produces yellow fluorescence on receiving that emission, which is sometimes referred to as blue-shifted-yellow (BSY). For instance, white light emitting diodes can be fabricated by forming a ceramic phosphor layer on the output surface of a blue light-emitting semiconductor light emitting diode. Part of the blue ray emitted from the light emitting diode chip passes through the phosphor, while part of the blue ray emitted from the light emitting diode chip is absorbed by the phosphor, which becomes excited and emits a yellow ray. The part of the blue light emitted by the light emitting diode which is transmitted through the phosphor is mixed with the yellow light emitted by the phosphor.

More specifically, a "BSY LED" refers to a blue LED and an associated recipient luminophoric medium that together emit light having a color point that falls within a trapezoidal "BSY region" on the 1931 CIE Chromaticity Diagram (FIG. 19) defined by the following x, y chromaticity coordinates: (0.32, 0.40), (0.36, 0.48), (0.43, 0.45), (0.42, 0.42), (0.36, 0.38), (0.32, 0.40), which is generally within the yellow color range, see for example, FIG. 5. A "BSG LED" refers to a blue LED and an associated recipient luminophoric medium that together emit light having a color point that falls within a trapezoidal "BSG region" on the 1931 CIE Chromaticity Diagram defined by the following x, y chromaticity coordinates: (0.35, 0.48), (0.26, 0.50), (0.13, 0.26), (0.15, 0.20), (0.26, 0.28), (0.35, 0.48), which is generally within the green color range. A "BSR LED" refers to a blue LED that includes a recipient luminophoric medium that emits light having a dominant wavelength between 600 and 720 nm in response to the light emitted by the blue LED. A BSR LED will typically have two distinct spectral peaks on a plot of light output versus wavelength, namely a first peak at the peak wavelength of the blue LED in the blue color range and a second peak at the peak wavelength of the luminescent materials in the recipient luminophoric medium when excited by the light from the blue LED, which is within the red color range. Typically, the red LEDs and/or BSR LEDs will have a dominant wavelength between 600 and 660 nm, and in most cases between 600 and 640 nm.

Figure 19:
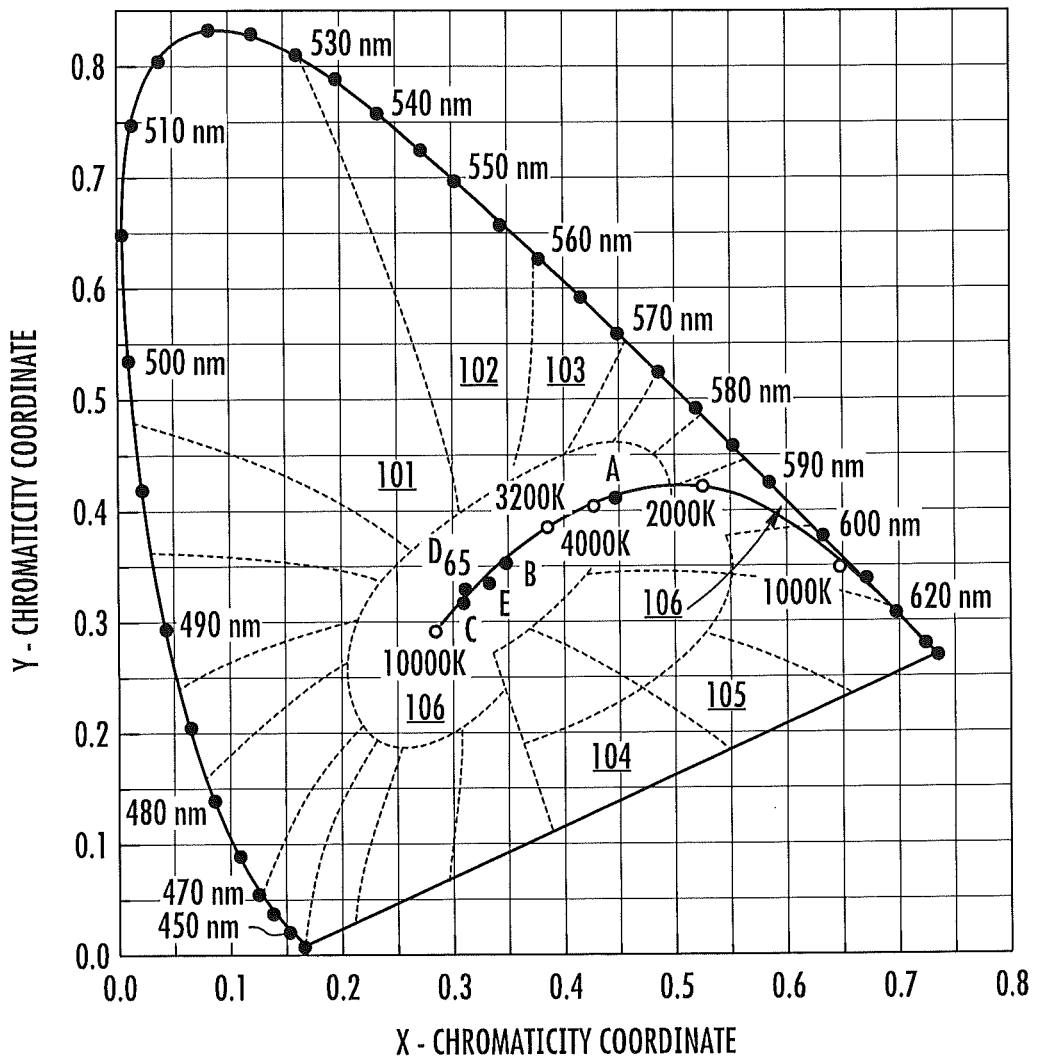
FIG. 19 is a 1931 CIE chromaticity diagram.

As shown in FIG. 19, colors on the 1931 CIE Chromaticity Diagram are defined by x and y coordinates (i.e., chromaticity coordinates, or color points) that fall within a generally U-shaped area. Colors on or near the outside of the area are saturated colors composed of light having a single wavelength, or a very small wavelength distribution. Colors on the interior of the area are unsaturated colors that are composed of a mixture of different wavelengths. White light, which can be a mixture of many different wavelengths, is generally found near the middle of the diagram, in the region labeled 106 in FIG. 19. There are many different hues of light that may be considered "white," as evidenced by the size of the region 106. For example, some "white" light, such as light generated by sodium vapor lighting devices, may appear yellowish in color, while other "white" light, such as light generated by some fluorescent lighting devices, may appear more bluish in color.

Light that generally appears green is plotted in the regions 101, 102 and 103 that are above the white region 106, while light below the white region 106 generally appears pink, purple or magenta. For example, light plotted in regions 104 and 105 of FIG. 5 generally appears magenta (i.e., red-purple or purplish red).

Also illustrated in FIG. 19 is the planckian locus 106, which corresponds to the location of color points of light emitted by a black-body radiator that is heated to various temperatures. In particular, FIG. 19 includes temperature listings along the black-body locus. These temperature listings show the color path of light emitted by a black-body radiator that is heated to such temperatures. As a heated object becomes incandescent, it first glows reddish, then yellowish, then white, and finally bluish, as the wavelength associated with the peak radiation of the black-body radiator becomes progressively shorter with increased temperature. Illuminants which produce light which is on or near the black-body locus can thus be described in terms of their correlated color temperature (CCT).

The chromaticity of a particular light source may be referred to as the "color point" of the source. For a white light source, the chromaticity may be referred to as the "white point" of the source. As noted above, the white point of a white light source may fall along the planckian locus. Accordingly, a white point may be identified by a correlated color temperature (CCT) of the light source. White light typically has a CCT of between about 2000 K and 8000 K. White light with a CCT of 4000 may appear yellowish in color, while light with a CCT of 8000 K may appear more bluish in color. Color coordinates that lie on or near the black-body locus at a color temperature between about 2500 K and 6000 K may yield pleasing white light to a human observer.

"White" light also includes light that is near, but not directly on the planckian locus. A Macadam ellipse can be used on a 1931 CIE Chromaticity Diagram to identify color points that are so closely related that they appear the same, or substantially similar, to a human observer. A Macadam ellipse is a closed region around a center point in a two-dimensional chromaticity space, such as the 1931 CIE Chromaticity Diagram, that encompasses all points that are visually indistinguishable from the center point. A seven-step Macadam ellipse captures points that are indistinguishable to an ordinary observer within seven standard deviations, a ten step Macadam ellipse captures points that are indistinguishable to an ordinary observer within ten standard deviations, and so on. Accordingly, light having a color point that is within about a ten step Macadam ellipse of a point on the planckian locus may be considered to have the same color as the point on the planckian locus.

The use of these types (and other) LEDs can promote truer color reproduction, which is typically measured using the Color Rendering Index (CRI). CRI is a relative measurement of how the color rendition of an illumination system compares to that of a blackbody radiator, i.e., it is a relative measure of the shift in surface color of an object when lit by a particular lamp. The CRI equals 100 if the color coordinates of a set of test colors being illuminated by the illumination system are the same as the coordinates of the same test colors being irradiated by the blackbody radiator. Daylight has the highest CRI (of 100), with incandescent bulbs being relatively close (about 95), and fluorescent lighting being less accurate (70-85). Certain types of specialized lighting have relatively low CRI's (e.g., mercury vapor or sodium, both as low as about 40 or even lower). Sodium lights are used, e.g., to light highways. Driver response time, however, significantly decreases with lower CRI values (for any given brightness, legibility decreases with lower CRI). Accordingly, the processor 720 can utilize, for example, CRI, color temperature, color values, CCT, etc. to determine values associated with the reflected light received by the electronic sensor 710, which can in turn be used to determine a $CO_2$ level. It will be understood that the $CO_2$ level can be determined by any approach, such as an equation or lookup table.

FIG. 8 is a schematic representation of a $CO_2$ detection system in some embodiments according to the invention. As shown in FIG. 8, the color change material 100 is located on an interior sidewall 801 of an adapter 807 configured to be removably coupled to a breathing circuit. For example, the adapter 807 is configured to be removably coupled to standard form-factor tubing typically used in systems such as ventilators, respirators, and other equipment used for medical procedures such as in operating rooms, emergency rooms, etc. The adapter 807 is further configured to allow the respiratory stream to flow longitudinally so that at least a portion of the respiratory gas conducted through the adapter 807 comes into contact with the surface of the color change material 100. It will be understood that due to the orientation and location of the color change material 100, the flow of respiratory gas is substantially unobstructed. Although the color change material 100 is shown attached to the sidewall 801, it will be understood that the color change material 100 can be located at any position within the interior of the adapter 807 while being longitudinally oriented as shown relative to the respiratory gas flow so as not to substantially impede the flow thereof.

An electronic emitter 805 is located outside the adapter 807 and is configured to emit visible light into the adapter 807 to illuminate the color change material 100 located on the adapter 807. An electronic sensor 810 is also located outside the adapter 807 and is configured to receive a portion of the light reflected by the color change material 100. As described herein, the change in the amount of $CO_2$ in the respiratory gases can cause a change in the pH of the color change material 100 thereby causing a shift in the color which can be detected using the electronic sensor 810 to determine the level of various light components of the visible light reflected by the color change material 100.

FIG. 9 is a schematic illustration of a $CO_2$ detection system in some embodiments according to the invention. According to FIG. 9, the color change material 100 is located on an interior surface 901 of an adapter 907. An electronic emitter 905 is located outside the adapter 907 opposite the color change material 100. The adapter 907 is configured to allow the respiratory gases to be conducted in a longitudinal direction while coming into contact with the surface of the color change material 100.

An electronic sensor 910 is located outside the adapter 907 behind the color change material 100 relative to the position of the electronic emitter 905. The electronic sensor 910 can be spaced apart from the outside surface of the adapter 907 by a spacer 912, which creates a space between a mounting for the sensor 910 and the surface: The space can be utilized to also accommodate filters (such as red, green, and blue filters) on the sensor 910, which can be used to promote the detection of those light components.

Accordingly, when the electronic emitter 905 emits visible light, the visible light impacts the color change material 100 but rather than reflecting from the surface to the sensor as described above in reference to, for example, FIG. 8, the visible light is detected by the electronic sensor 910 located on the opposing side of the color change material 100 on the outside of the adapter 907. It will be understood that the electronic sensor 910 can be used to determine the relative levels of $CO_2$ in the respiratory stream as described herein.

Figure 10:
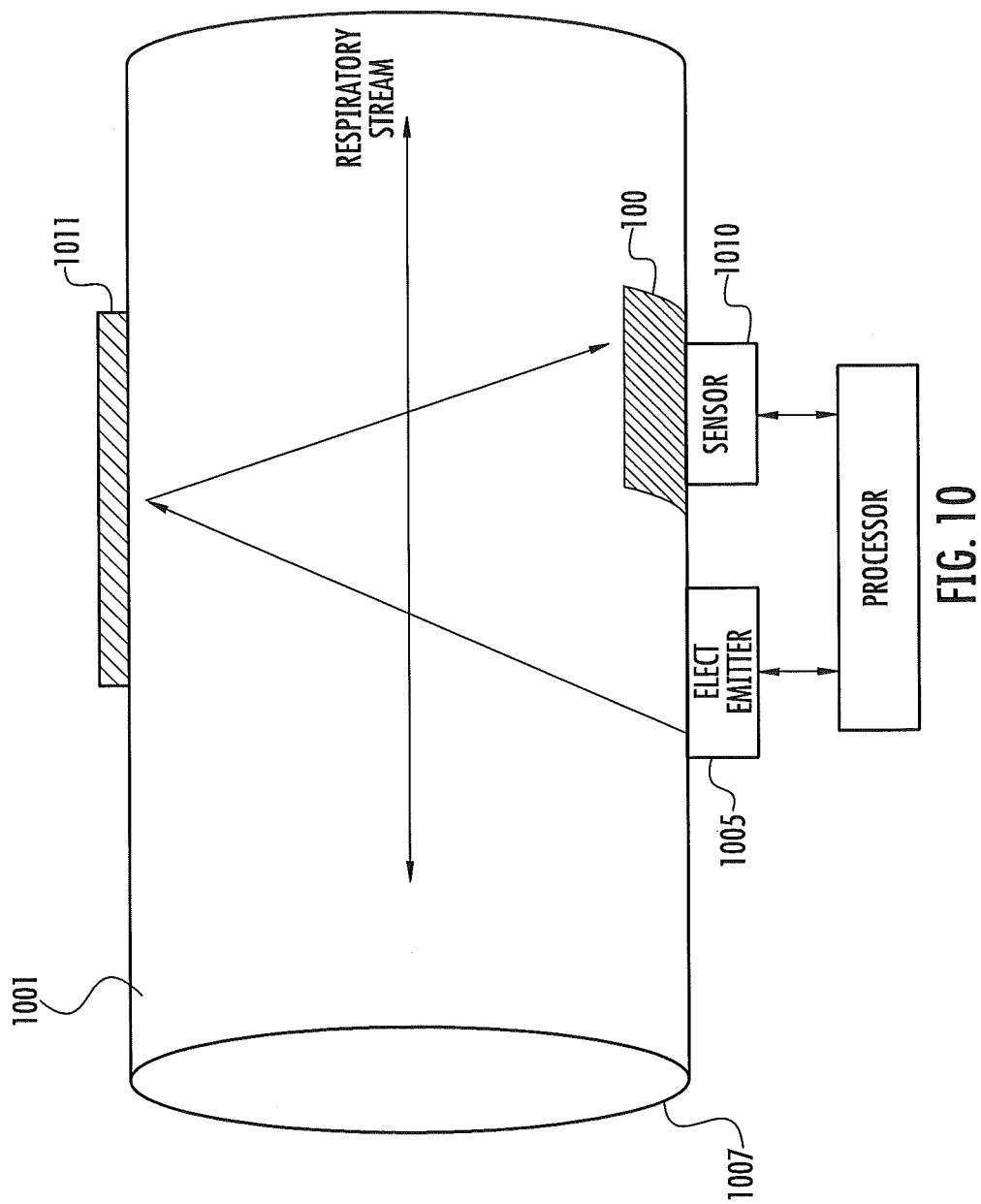
FIG. 10 is a schematic representation of a $CO_2$ detection system in some embodiments according to the invention.

FIG. 10 is a schematic illustration of a $CO_2$ detection system in some embodiments according to the invention. According to FIG. 10, the color change material 100 is located on an interior surface 1001 of an adapter 1007 and is configured to allow the respiratory stream of gases to come into contact therewith without substantially restricting the flow thereof. As further shown in FIG. 10, a reflector 1011 is located outside the adapter 1007 on an opposing side thereof relative to the color change material 1100. An electronic emitter 1005 located outside the adapter 1007 and emits visible light to impact the reflector 1011 which is reflected onto the color change material 1100 as shown. The visible light reflected onto the color change material 100 is detected using an electronic sensor 1010 located outside the adapter 1007 on an opposing side thereof relative to the reflector 1011. It will be understood that the relative levels of $CO_2$ in the respiratory gas stream can be determined as described herein.

Figure 11:
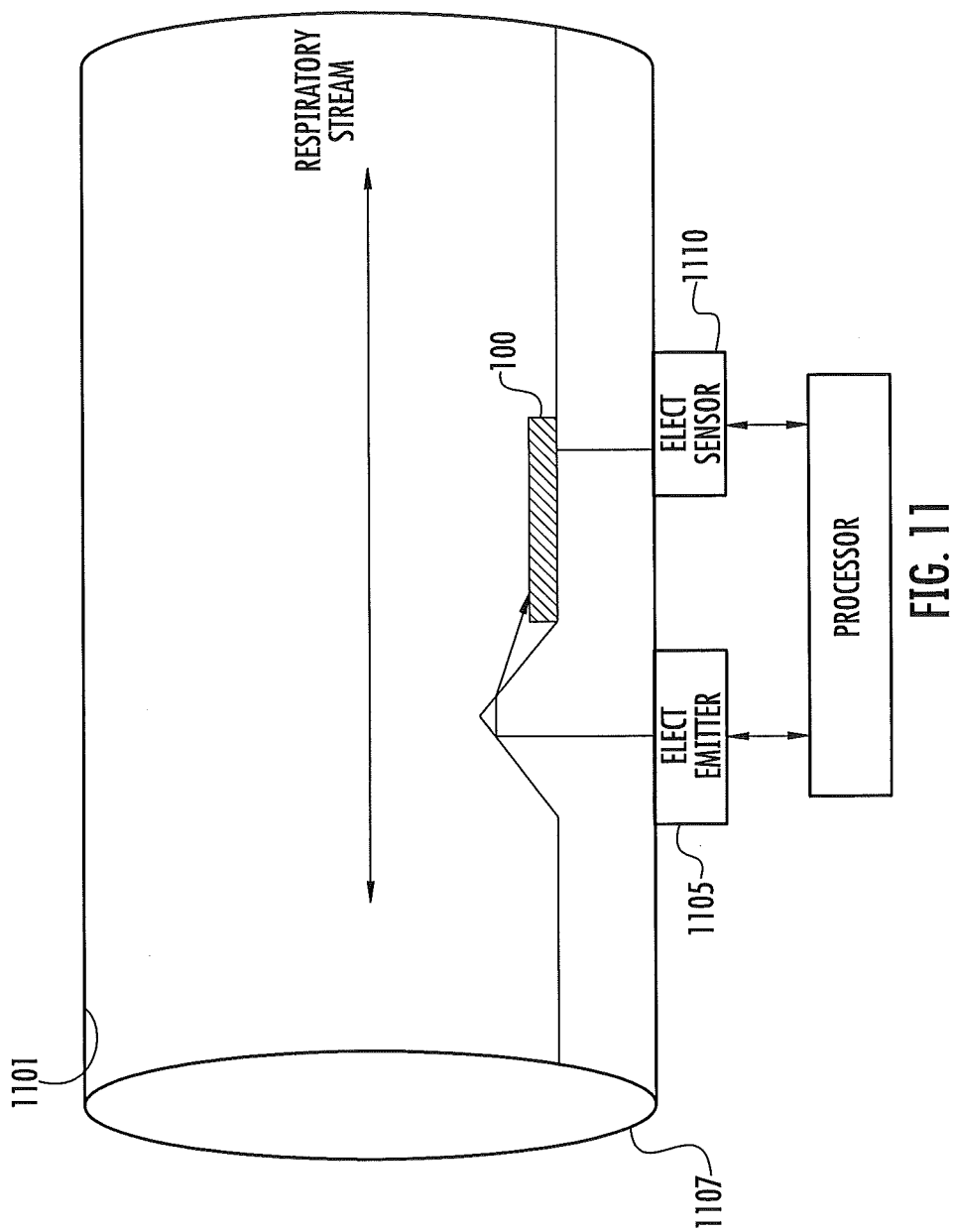
FIG. 11 is a schematic representation of a $CO_2$ detection system in some embodiments according to the invention.

FIG. 11 is a schematic illustration of a $CO_2$ detection system in some embodiments according to the invention. According to FIG. 11, a color change material 100 is located on an interior surface 1101 of an adapter 1107. The color change material 100 is configured within the adapter 1107 to allow the respiratory gas stream conducted therein to come into contact therewith while not substantially obstructing the flow of respiratory gases. As further shown in FIG. 11, the sidewall of the adapter 1107 includes an optical path configured to refract visible light emitted by an electronic emitter 1105 onto the surface of the color change material 100. The visible light reflected onto the color change material 100 can be detected by an electronic sensor 1110. It will be understood that the relative levels of $CO_2$ in the respiratory gas stream can be determined based on the approaches described herein.

Figure 12:
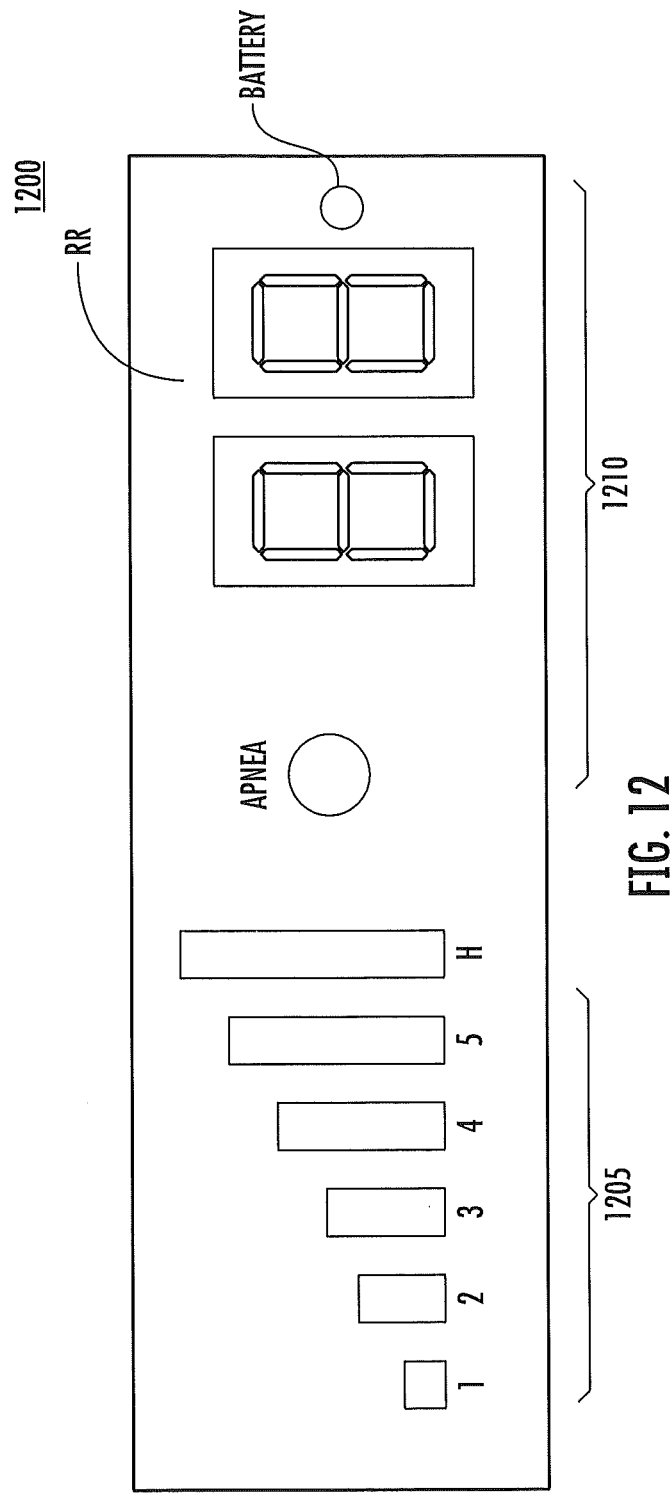
FIG. 12 is a schematic illustration of a display configured to provide information regarding $CO_2$ provided by the $CO_2$ system in some embodiments according to the invention.

FIG. 12 is a schematic representation of an exemplary display included in a $CO_2$ detection system in some embodiments according to the invention. According to FIG. 12, a $CO_2$ level portion of the display 1205 indicates the level of $CO_2$ in the respiratory stream based on the electronic sensors processing of the color components included in the reflected visible light. An auxiliary portion of display 1210 can include other information regarding the status of the subject. For example, auxiliary information 1210 may include a read out RR which indicates respiration rate, an indicator light signaling an apnea condition, and a battery level indicator.

Figure 13:
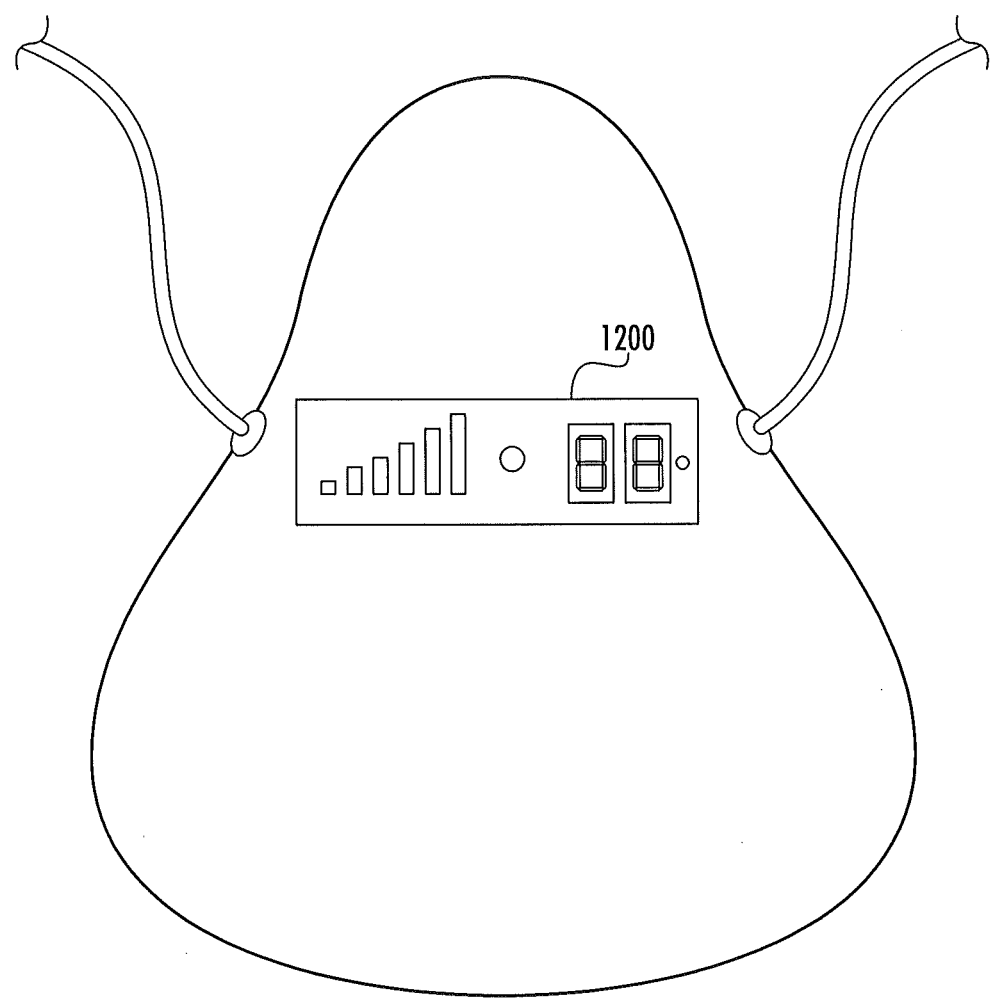
FIG. 13 is a schematic illustration of a mask incorporating a display configured to provide $CO_2$ information provided by the $CO_2$ system in some embodiments according to the invention.

FIG. 13 is a schematic representation of a mask configured for placement over a subject's mouth and nose and including the display 1200 shown in FIG. 12. Although the display 1200 is shown located at a bridge portion of the mask, it will be understood that the display 1200 can be located in any orientation or location of the mask which facilitates its use in a particular environment. In particular, for example, in some embodiments according to the invention, the display 1200 may be located on a side portion of the mask.

Figure 14:
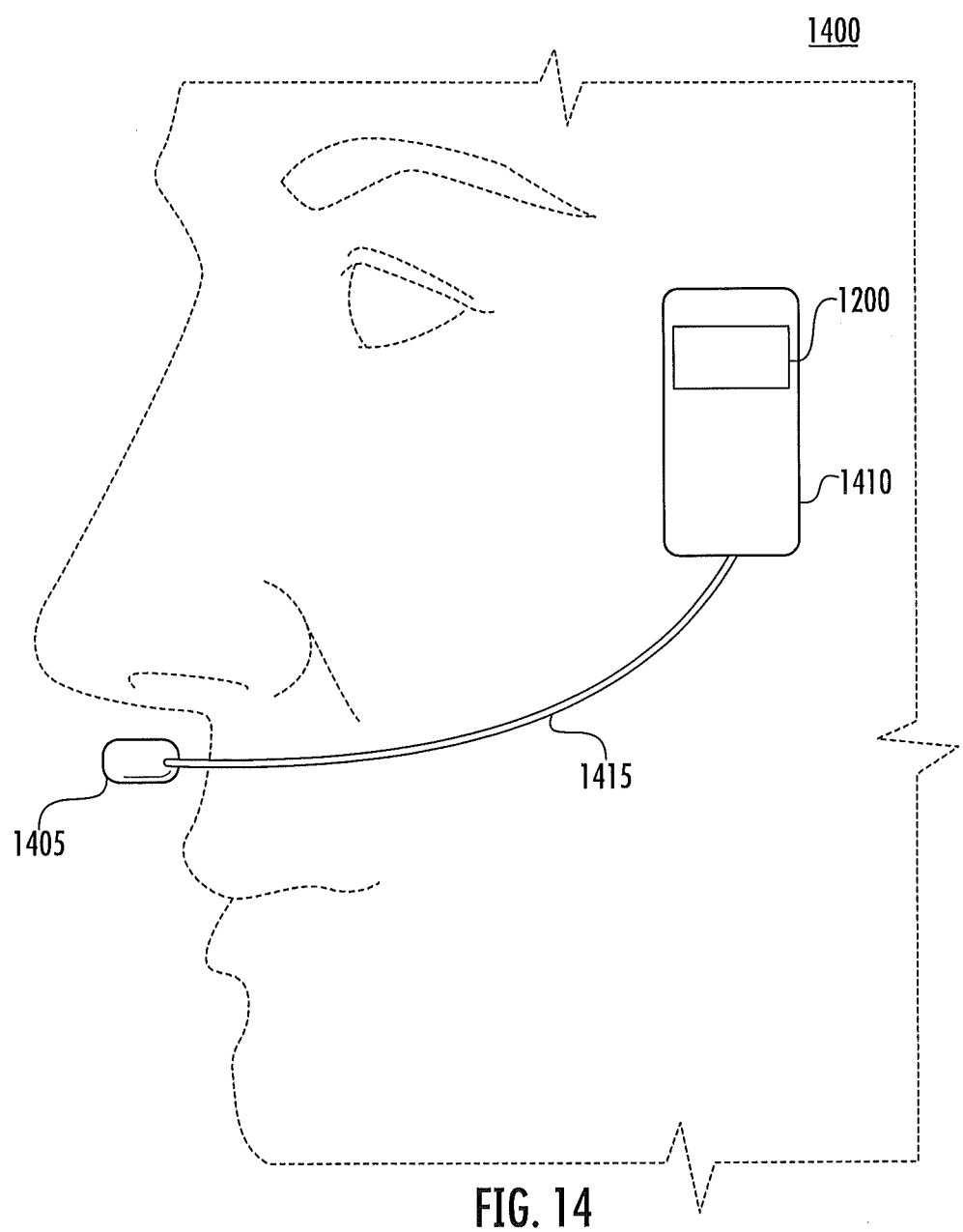
FIG. 14 is a schematic illustration of a $CO_2$ detection system utilized in an open breathing environment in some embodiments according to the present invention.

FIG. 14 is a schematic representation of a $CO_2$ detection system configured for operation in an open breathing environment in some embodiments according to the invention. According to FIG. 14, the color change material 100 along with the electronic emitter and a sensor as described herein can be located in an open environment. For example, adjacent to a subject's nose and/or mouth and not enclosed within, for example, the adapter shown in FIG. 8. According to FIG. 14, an open environment $CO_2$ detection system 1400 includes a sensor portion 1405 that can include the color change material 100 described herein. The sensor portion can also include a transmit/receive system which allows for the transmission of visible light from an emitter that is located remote from the sensor portion 1405. The transmit/receive system can also include a receiver that provides for the reflected visible light to be provided to an electronic sensor that is remote from the sensor portion 1405.

The $CO_2$ detection system 1400 also includes an electronic portion 1410 that can include the electronic emitter and electronic sensor in communication with the sensor portion 1405 via a transmission medium 1415 located therebetween. It will be understood that the electronics portion 1410 can also include a display such as that shown in FIG. 12 in some embodiments according to the invention. In operation, when the subject breathes in the open environment, sufficient $CO_2$ may be brought into contact with the color change material located in the sensor portion 1405 despite the fact that it is not enclosed within a breathing circuit as described herein. The remote electronics portion 1410 can be in communication with the sensor portion 1405 via the transmission media 1415 to provide the same determination of $CO_2$ levels included in the respiratory stream in the open environment.

Figure 15A:
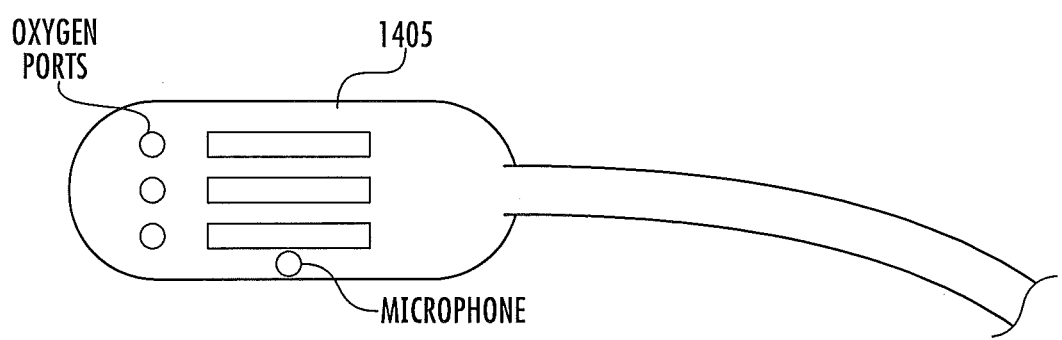
FIG. 15A is a greater detail schematic illustration of the $CO_2$ detection system shown in FIG. 14 in some embodiments according to the invention.
Figure 15B:
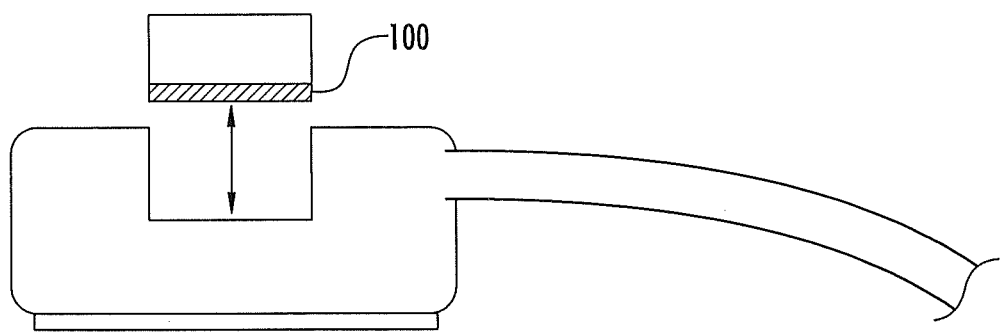
FIG. 15B is a greater detail schematic illustration of the $CO_2$ detection system shown in FIG. 14 in some embodiments according to the invention.

FIGS. 15A and 15B are different views of the $CO_2$ detection system 1400 shown in FIG. 14. According to FIG. 15A, the sensor portion 1405 can include ports that allow for the exhaled $CO_2$ to be in contact with the color change material located within. In addition, the sensor portion 1405 can include other features, such as, a microphone, oxygen ports, and other modalities and/or sensors. As shown in FIG. 15B, the color change material 100 may be included as part of an apparatus that is removably coupled to the sensor portion 1405. For example, the color change material 100 may be included as part of a cartridge that is inserted into the rear of the sensor portion 1405 so that the $CO_2$ detection system 1400 is not required to be removed from the subject for replacement of the color change material 100 such as when the buffer included in the color change indicator is depleted to the point where inaccurate $CO_2$ levels may be reported. Accordingly, other services to the subject, such as oxygen and other features may be uninterrupted while the $CO_2$ sensor color change material 100 is replaced.

Figure 16:
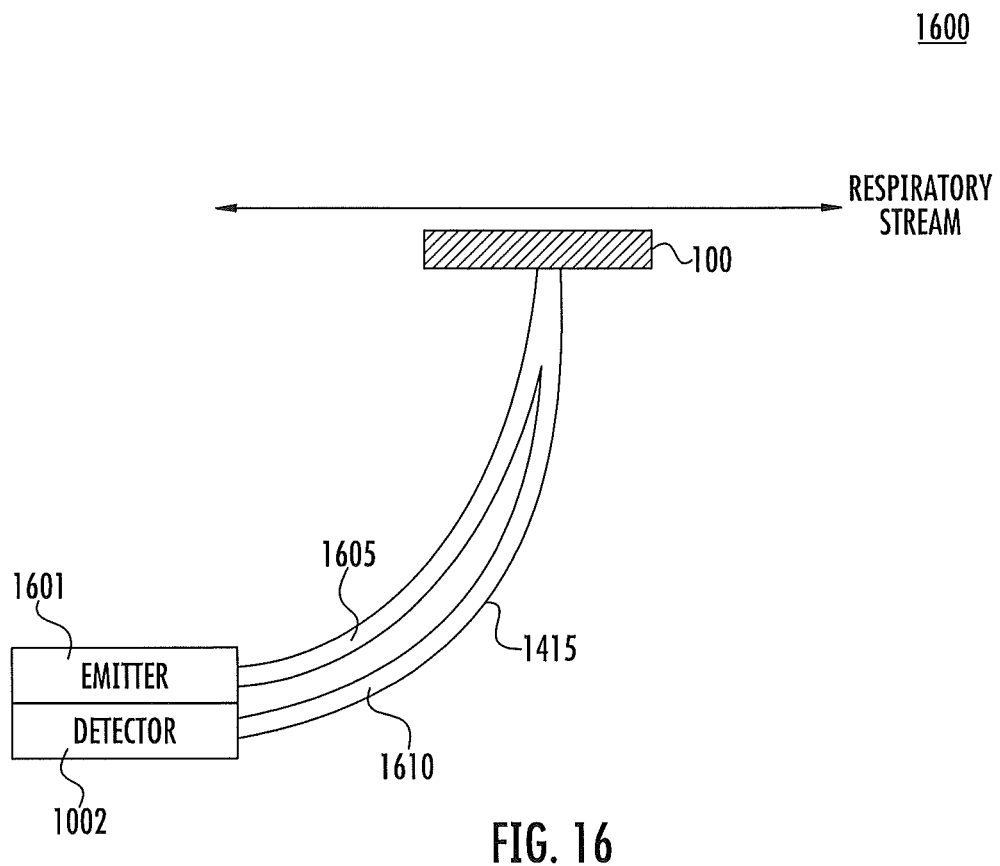
FIG. 16 is a schematic illustration of the $CO_2$ detection system including optical components in some embodiments according to the invention.

FIG. 16 is a schematic representation of an optical implementation of the $CO_2$ detection system 1400 shown in FIG. 14. According to FIG. 16, the color change material 100 can be located proximate to the respiratory stream as shown, for example, in FIG. 14 within the sensor portion 1405. The transmission medium 1415 can be provided by an optical cable that allows for the electronic emitter to provide the visible light to the color change material 100 via a first channel of the transmission medium, the first optical channel 1605 whereas the electronic sensor is provided with the reflected visible light via a second optical channel 1610. It will be understood that other types of transmission mediums may also be used.

It is also noted that circuitry designed for detecting $CO_2$ levels or other types of compounds may be small enough to be housed in a portable unit operating under battery power. The advantages of having a portable unit are numerous but may include availability in remote locations under in-the-field conditions. This may allow the detector to be provided to all EMT's, first responders, military units, police personnel and the like. Various types of batteries may be used to generate sufficient power to detect the presence of $CO_2$ as well as operate any type of display or data transmission. Other power sources can also be used.

Furthermore, the $CO_2$ detection system can be designed to be an all-in-one unit designed to display data or measurements at the actual point of measurement, which would be a display incorporated as part of the device that attaches to the endotrachael tube, ventilating mask, or source of the exhaled gases intended to be tested for the presence of $CO_2$. An alternative method would allow for remote monitoring of the collected data or measurements, via wireless connection to either a specifically designed, purpose built base unit which could either be hand held or bench top in nature, or via a specific application/app written to be used on a smart phone platform.

Figure 17:
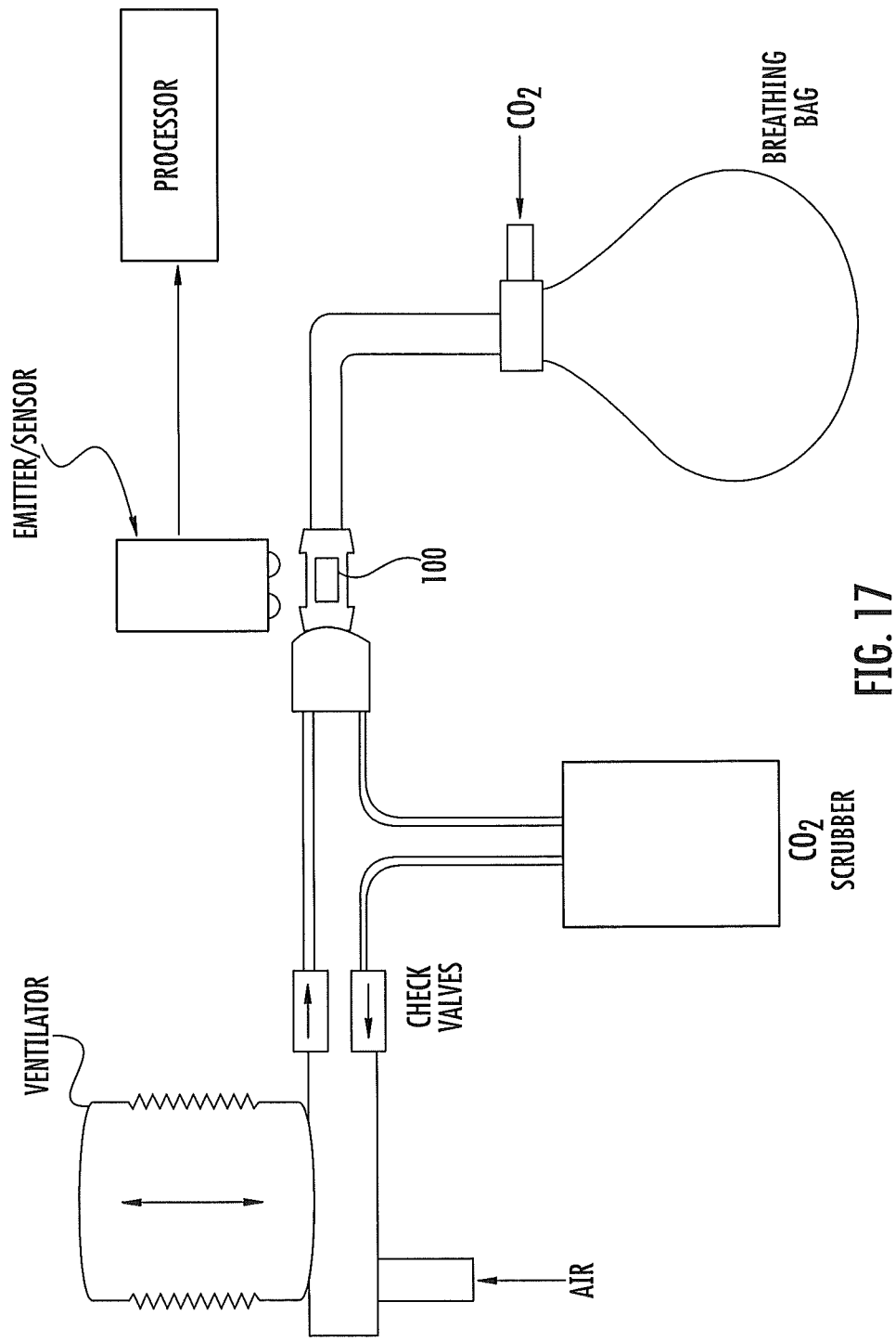
FIG. 17 is a schematic illustration of test setup for a $CO_2$ detection system in some embodiments according to the invention.
Figure 18:
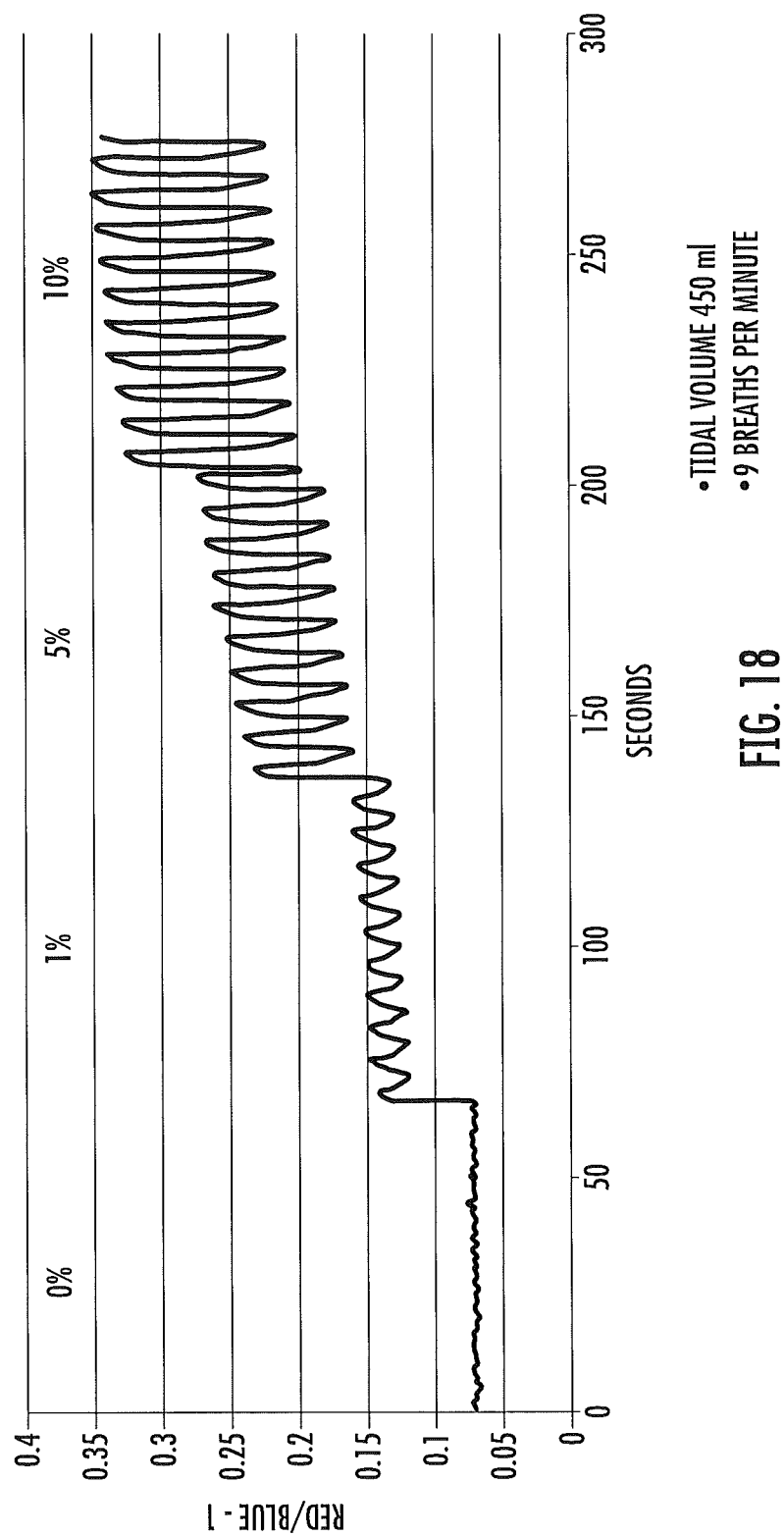
FIG. 18 is a graph illustrating $CO_2$ information generated by the $CO_2$ detection system operating in the test setup shown in FIG. 17.

FIG. 17 is a schematic illustration of test setup for a $CO_2$ detection system in some embodiments according to the invention. FIG. 18 in a graph illustrating $CO_2$ information generated by the $CO_2$ detection system operating in the test setup of FIG. 17.

Carbon dioxide detector 1 was configured inside of a 21 mm adapter tube commonly used as a connector fitting in medical airway circuits. The color change material was mounted such that air flow within the tube was substantially parallel to the surface of the color change material, and the color change material was at a position approximately equatorial within the tube. The colorimetrically active surface of the color change material was illuminated from outside of the tube using a multicolor LED device containing a red, a green, and a blue LED in a surface mount package. A color sensing device was mounted adjacent the LED outside of the tube. The color sensing device was aimed at the surface of the color change material to intercept a portion of light reflected from its surface. The color sensing device was electronically configured to provide digital signals representative of the relative portions of red, green, and blue light in the reflected light.

Gas within the tube comprised a mixture of air and carbon dioxide, the relative proportions of which could be varied. The breathing circuit was connected to a respirator to simulate human breathing at 10 breaths per minute and a volume flow of 4 liters per minute. The gas circuit was configured to route gases through a "polysorb" carbon dioxide scrubber during the exhalation portion of the breathing cycle. This removed all $CO_2$ in the gas stream. $CO_2$ was mixed in a portion of the circuit to mimic production of $CO_2$ during an exhalation cycle. The "exhaled" breath was passed through the tube containing the color change material, and then routed to the scrubber. While breathing various mixtures of carbon dioxide that were intentionally varied from below normal physiological levels to above normal levels, data were recorded from the digital outputs of the color sensor device and plotted over time, as shown in FIG. 18. The plot showed that the average ratio of red color to blue color varied in proportion to the carbon dioxide content in the breath stream. The plot also showed that breath-to-breath differences in carbon dioxide could be recorded. Data was found to provide an accurate calibration of carbon dioxide content and respiratory rate.

In further embodiments according to the invention, the color change material 100 can include at least two portions where at least one portion is reactive to $CO_2$ exposure whereas another portion is unreactive to the $CO_2$. Accordingly, the reactive portion can be configured to change color responsive to the $CO_2$ level in the respiratory stream. The unreactive portion, however, may not change color (or may exhibit a lesser change in color compared to the reactive portion) so that the unreactive portion can be used to provide a control signal to the processor circuit. The control signal can be used, for example, to monitor the functionality of the color change material 100 over time.

As the color change material 100 is repeatedly exposed to the respiratory stream over time, the color change exhibited by the reactive portion can be reduced despite being exposed to the same level of $CO_2$ in the respiratory stream. Accordingly, the reactive portion of the color change material 100 may provide a less accurate indication of the $CO_2$ level. As appreciated by the present inventors, the color exhibited by the unreactive portion can be compared to the color change exhibited by the reactive portion in response to the $CO_2$ level in the respiratory stream. If the difference between the colors is less than a predetermined threshold, a signal can be generated to indicate that the functionality of the color change material 100 may be ineffective.

In some embodiments according to the invention, the circuits operatively coupled to the color change material 100 can include multiple visible light sensor circuits. For example, in some embodiments according to the invention, the visible light can be emitted into the breathing circuit to impinge upon the reactive and unreactive portions of the color change material. A first visible light sensor circuit can be operatively coupled to the reactive portion of the color change material 100, whereas a second visible light sensor circuit can be operatively coupled to the unreactive portion of the color change material 100. This type of arrangement can allow the monitoring of the color change exhibited by the reactive portion over time as described above. In some embodiments according to the invention, the first and second visible light sensor circuits are separately controlled by the processor circuit.

The color change material 100 can be separated into different-portions so that the emitted visible light impinging on the reactive portion does not affect the second visible light sensor circuit and the visible light impinging on the unreactive portion does not affect the first visible light sensor circuit. In other words, the configuration of the color change material 100 may shield each of the respective sensor circuits from unwanted portions of the emitted visible light.

In still further embodiments according to the invention, one of the visible light sensor circuits may be utilized to detect an ambient light level in the breathing circuit. In operation, the processor circuit may receive the ambient light component from one of the visible light sensor circuits as a control signal, which may be utilized to compensate for the ambient light component detected by the other visible light sensor circuit.

Figure 20:
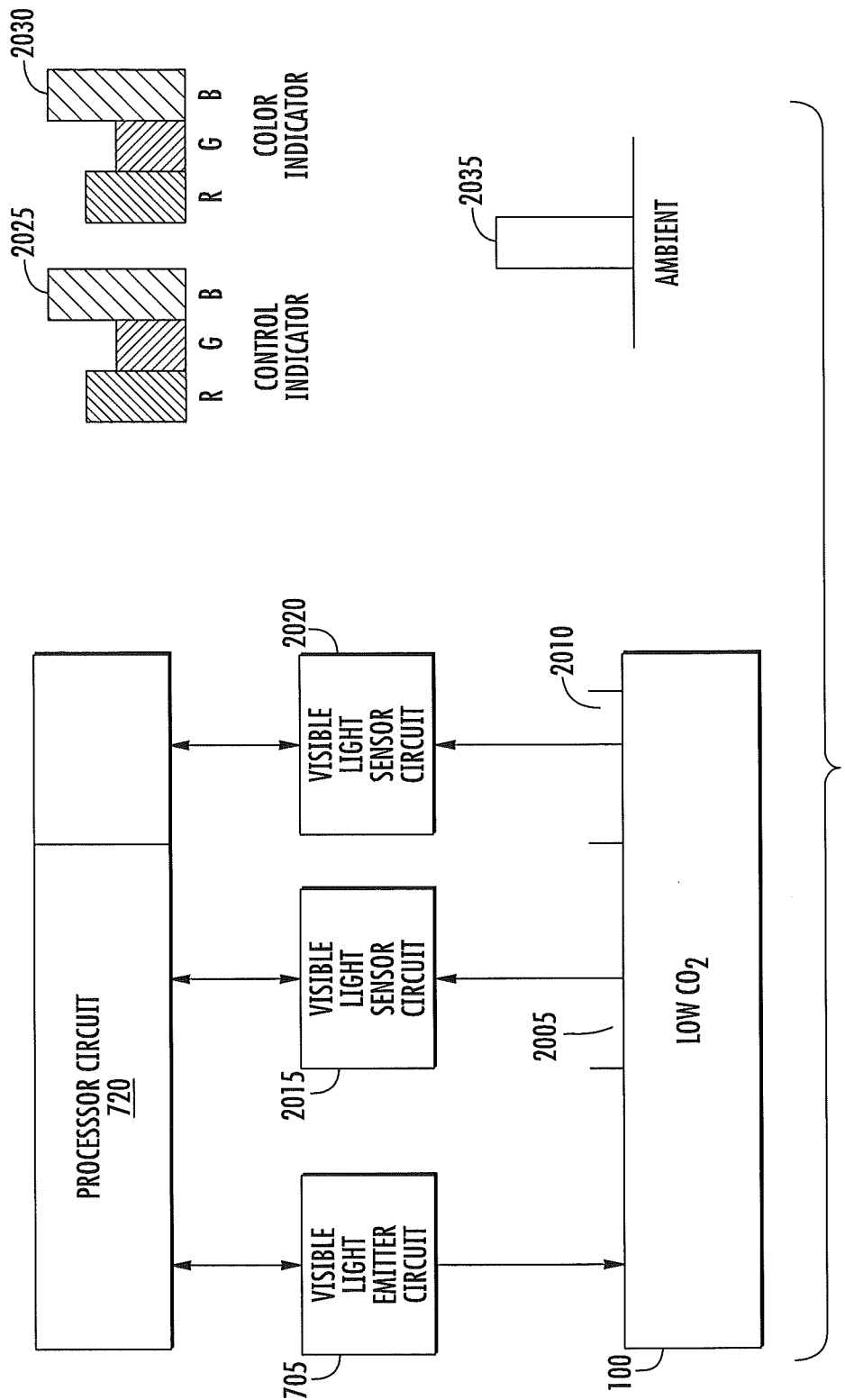
FIG. 20 is a schematic representation of a color change material included in a breathing circuit and exposed to electronically generated visible light and electronic sensing thereof in some embodiments according to the invention.

FIG. 20 is a schematic representation of a color change material 100 included in a breathing circuit and exposed to electrically generated visible light and electronic sensing thereof in some embodiments according to the invention. Specifically, FIG. 20 illustrates that the color change material 100 is exposed to a relatively low $CO_2$ level in the respiratory stream conducted by the breathing circuit. A first visible light sensor circuit 2015 is operatively coupled to a reactive portion 2005 of the color change material 100, whereas a second visible light sensor circuit 2020 is operatively coupled to an unreactive portion 2010 of the color change material 100. In operation, when the visible light emitter circuit 705 emits visible light onto the color change material 100, the first visible light sensor circuit 2015 detects a first portion of the emitted visible light that passes through the reactive portion 2005, whereas the second visible light sensor circuit 2020 detects a second portion of the emitted visible light that passes through the unreactive portion 2010.

Because the relatively low level of $CO_2$ elicits a particular color response from the reactive portion 2005, the visible light sensor circuit 2015 provides a reactive signal to the processor circuit 720. In contrast, the second visible light sensor circuit 2020 generates a control signal to the processor circuit that represents little (or at least reduced) color change relative to that provided by the reactive portion 2005 when exposed to the relatively low level of $CO_2$.

As further shown in FIG. 20, the components of the color indication 2030 are associated with the reactive signal generated by the first visible light sensor circuit 2015 whereas the components of the color control indication 2025 show the color components included in the control signal generated by the second visible light sensor circuit 2020. It will be understood that because of the relatively low $CO_2$ level shown in FIG. 20, the color indication 2030 and the color control indication 2025 may be substantially identical to each other.

As further shown in FIG. 20, the second visible light sensor circuit 2020 can also be utilized to determine an ambient light control component 2035. In operation, the processor circuit 720 may provide the ambient light control component 2035 by summing the individual components of the color control indication 2025. In other embodiments according to the invention, the processor circuit 720 may access a separate portion of the sensor circuit 2020, such as a clear channel, to provide the ambient light control component 2035. The processor circuit 720 can compensate the color indication 2030 using the ambient light control component 2035. In some embodiments according to the invention, the ambient light control component 2035 may be subtracted from the color indication 2030 to provide a more accurate indication of only the portion of the emitted visible light detected by the first visible light sensor circuit 2015 (by reducing the influence of the ambient light on the color indication 2030). It will be understood that in some embodiments according to the invention, the ambient component 2035 can be provided using either of the sensor circuits or by another sensor circuit.

Figure 21:
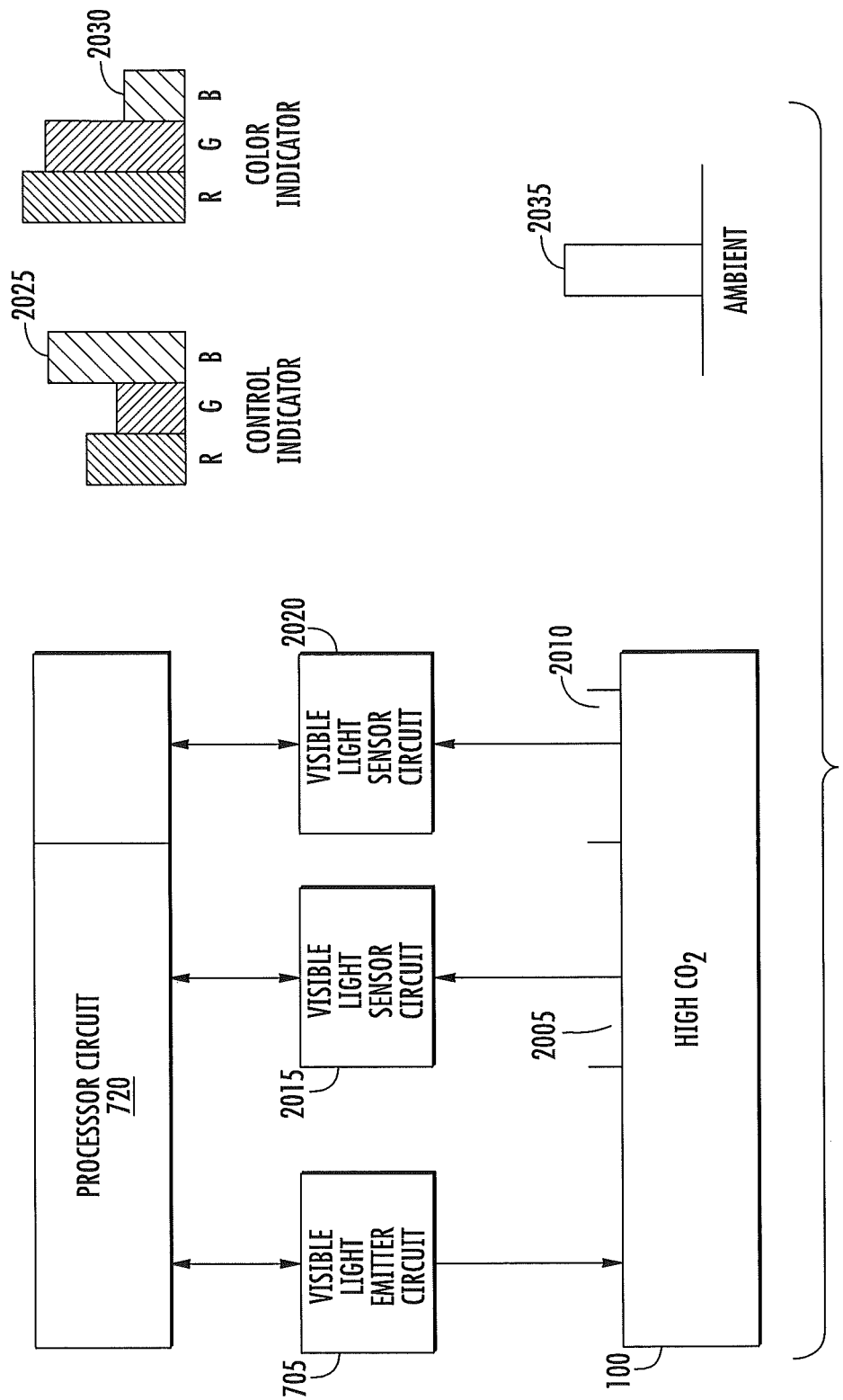
FIG. 21 is a schematic representation of a color change material included in a breathing circuit and exposed to electronically generated visible light and electronic sensing thereof in some embodiments according to the invention.

FIG. 21 is a schematic representation of a color change material included in a breathing circuit and exposed to electronically generated visible light and electronic sensing thereof in some embodiments according to the invention. According to FIG. 21, the color change material 100 is exposed to a relatively high $CO_2$ level in the respiratory stream conducted by the breathing circuit as a part of a respiratory cycle. As further illustrated in FIG. 21, because of the increase in the $CO_2$ level detected by the color change material 100, the color indication 2030 changes from that shown in FIG. 20, whereas the color control indication 2025 provided by the unreactive portion 2010 may remain the same as that shown in FIG. 20 (i.e., the relatively low $CO_2$ level environment).

In operation, the processor circuit 720 can compare the color control indication 2025 provided by the unreactive portion 2010 to the color indication 2030 provided by the reactive portion 2005. If the processor circuit 720 determines that the color indication 2030 is exhibiting less color change than expected in a high $CO_2$ level environment, the processor circuit can provide a signal that maintenance of the color change material 100 should be performed. For example, the processor circuit 720 may indicate that the color change material 100 should be changed.

As appreciated by the present inventors, as the color change material 100 is repeatedly utilized, the reactive nature of the color change material may be depleted due to repeated exposure to the respiratory stream. Therefore, and in order to provide more accurate results over time, the color change material 100 may be replaced with a fresh color change material 100 if a predetermined threshold is reached. As further appreciated by the present inventors, the color control indication 2025 can be utilized as a "base line" to indicate the color that exhibited by the reactive portion 2005 in a functional (or original) state. In other words, the color control indication 2025 can correspond to a known good color that reactive portion 2005 should exhibit when in the breathing circuit. Over time, as the color change material 100 is exposed to the $CO_2$ in the respiratory stream, the color change exhibited by the reactive portion 2005 may be reduced, and therefore, may more closely resemble the color control indication 2025 associated with the unreactive portion 2010.

As further shown in FIG. 21, the processor circuit 720 can utilize the second visible light sensor circuit 2020 to provide the ambient light control component 2035 which may be used to adjust the color indication 2030 provided by the first visible light sensor circuit 2015, so that the processor circuit 720 may determine a more accurate indication of the $CO_2$ level to which the color change material 100 is exposed by reducing the contribution from ambient light. Other circuits can also be used to provide the ambient light component.

Figure 22:
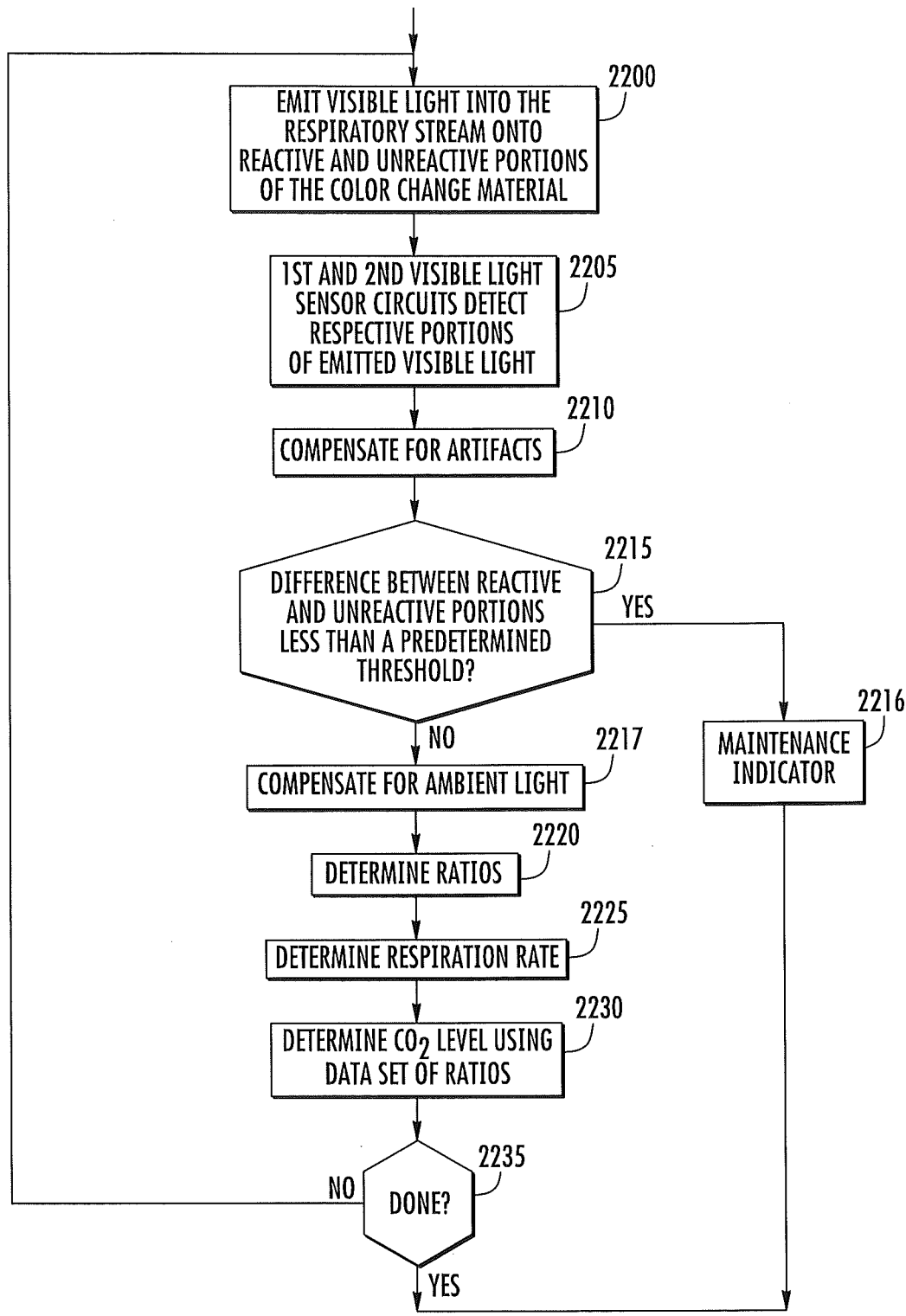
FIG. 22 is a flowchart illustrating operations of a $CO_2$ detection system including a color change material operatively coupled to a visible light emitter circuit and visible light sensor circuits in some embodiments according to the invention.

FIG. 22 is a flowchart that illustrates operations of a $CO_2$ level detection system in some embodiments according to the invention. According to FIG. 22, the processor circuit 720 controls the visible light emitter circuit to emit visible light into the breathing circuit into the respiratory stream and through the color change material to impinge on the first and second visible light sensor circuits 2015 and 2020 (block 2200). The first and second visible light sensor circuits 2015 and 2020 detect the respective colors generated by the reactive portion 2005 and the unreactive portion 2010 (blocks 2205). It will be further understood that the reactive portion 2005 can change color in response to exposure to the $CO_2$ in the respiratory stream whereas the unreactive portion 2010 exhibits less color change.

The processor circuit 720 can access the data generated by the first and second visible light sensor circuits 2015 and 2020. In particular, the processor circuit 720 can receive color indications in the form of color components from each of the first and second visible light sensor circuits 2015 and

2020. For example, the processor circuit 720 can access the first visible light sensor circuit 2015 to retrieve red, green, and blue color components for the color exhibited by the reactive portion 2005. Similarly, the processor circuit 720 can retrieve red, green, and blue color components from the second visible light sensor circuit 2020 with the indication of the color generated by the unreactive portion 2010.

The processor circuit 720 can also utilize the color components to compensate for adverse artifacts that may otherwise impact the determination of the $CO_2$ level exhibited by the color change material 100 (block 2210). For example, the processor circuit 720 can compare the color components associated with the reactive portion 2005 to the color components associated with the unreactive portion 2010 (block 2215). If the difference between these two sets of color components is less than a predetermined threshold the processor circuit 720 may determine that the reactive portion 2005 is, for example, beyond its useful life and should be replaced. In particular, the reactive portion 2005 may be saturated with $CO_2$ due to prolonged exposure to the respiratory stream and therefore should be replaced. In still other embodiments according to the invention, the processor circuit 720 can use the comparison of color components as described herein to provide an initial indication of whether the reactive portion 2005 is adequate for an accurate determination of the $CO_2$ level. Still further, over time the processor circuit 720 can use the comparison of the color components associated with the reactive and unreactive portions 2005 and 2010, to monitor the "wear" on the color change material 100.

If the processor circuit 720 determines that the reactive portion 2005 is past its useful lifetime (Block 2215) the processor circuit 720 can generate a maintenance indicator signaling that the color change material (or at least the reactive portion 2005) should be replaced. Still further, operations of the $CO_2$ level detection system in some embodiments according to the invention may cease until a functional color change material 100 is provided and tested by the processor circuit 720 during initialization. If, however, the processor circuit 720 determines that the functionality of the reactive portion 2005 is adequate (Block 2215), the processor circuit 720 may also compensate for ambient light detected within the breathing circuit (block 2217). For example, the processor circuit 720 may determine the ambient light control component 2035 by accessing a clear channel associated with the second visible light sensor circuit 2020. In other embodiments according to the invention, the processor circuit 720 may combine the color control components 2025 to provide an indication of the ambient light. The processor circuit 720 may then compensate for the ambient light to reduce any adverse artifacts associated with ambient light in the breathing circuit to provide a more accurate indication of the true color generated by the reactive portion 2005 and thereby a more accurate indication of the $CO_2$ level in the respiratory stream.

The processor circuit 720 can then determine ratios of components in the color indication 2030 to one another and ratios of components in the color control indication 2025 to one another. For example, in some embodiments according to the invention, the processor circuit 720 may provide a ratio of the red component divided by the green component for each of the color control indications 2025 and the color indications 2030 collected over time (block 2220).

It will be understood that the processor circuit 720 can be configured to sample the color control indication 2025 and the color indication 2030 at least ten times per second in order to determine a respiration rate based on the ratios generated by the processor circuit 720 (Block 2225). For example, the processor circuit 720 can repeatedly sample the data provided by the first and second visible light sensor circuits 2015 and 2020 until an adequate data set is generated where the data set includes the ratios described above. The value of the ratios can then be examined over time to determine the respiration rate of the respiratory stream. In particular, the processor circuit 720 can be configured to locate three directly adjacent minimum or maximum values for the ratios to identify at least one cycle of respiration within the respiratory stream. The timing between the minimum or maximum ratio values can be used to determine the respiration rate.

The processor circuit 720 is configured to determine the $CO_2$ level in the respiratory stream using the data set including the ratio values described above (block 2230). For example, in some embodiments according to the invention, the processor circuit 720 may examine the data set to calculate the peak-to-peak value that represents the difference between the minimum ratio value within the cycle and the maximum ratio value within the cycle. In some embodiments according to the invention, the processor circuit 720 is configured to determine the $CO_2$ level based on the ratio values associated with the first visible light sensor circuit 2015 (having been compensated with the ambient light control component). In still other embodiments according to the invention, the processor circuit 720 is configured to determine the $CO_2$ level based on a combination of the peak-to-peak ratio value and the minimum value of the ratio associated with the first visible light sensor circuit 2015. In still further embodiments according to the invention, the processor circuit 720 is configured to determine the $CO_2$ level utilizing the peak-to-peak value approach more heavily during relatively low respiratory rates, whereas the minimum ratio value may be more heavily weighted during periods of higher respiratory rates. Operations can continue as described above as long as the respiratory stream is supplied to the breathing-circuit and/or at least the reactive portion 2005 is deemed functional by the processor circuit 720 (block 2235).

Figure 23:
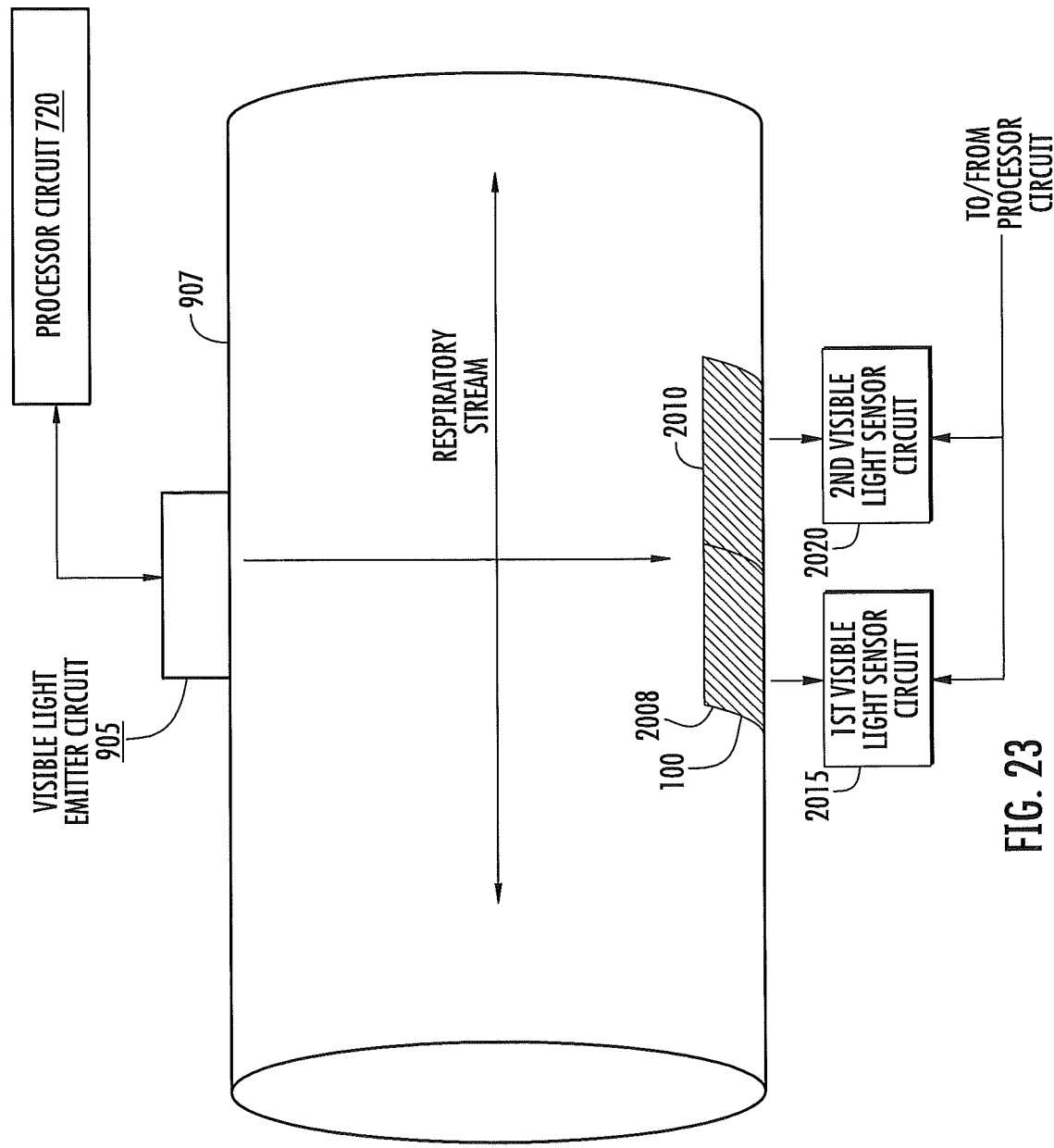
FIG. 23 is a schematic representation of a color change material included in a breathing circuit and exposed to electronically generated visible light and electronic sensing thereof in some embodiments according to the invention.

FIG. 23 is a schematic representation of the color change material 100 included in a breathing circuit and exposed to electronically generated visible light and electronic sensing thereof in some embodiments according to the invention. According to FIG. 23, the processor circuit 720 controls the visible light emitter circuit 905 to emit visible light into the breathing circuit 907 that conducts the respiratory stream. The emitted visible light passes through the respiratory stream and impinges on the color change material 100.

The color change material 100 includes the reactive portion 2005 and the unreactive portion 2010 that is spaced apart from the reactive portion 2005. The first visible light sensor circuit 2015 is positioned proximate to the reactive portion 2005 and the second visible light sensor circuit 2020 is positioned proximate to the unreactive portion 2010. In operation, a first portion of the emitted visible light passes through the reactive portion 2005 and impinges on the first visible light sensor circuit 2015. In contrast, a second portion of the emitted visible light passes through the unreactive portion 2010 and impinges on the second visible light sensor circuit 2020.

It will be understood that the first and second visible light sensor circuits 2015 and 2020 are positioned relative to the reactive and unreactive portions 2005 and 2010 to reduce artifacts attributable to that portion of the emitted visible light which is provided to the other sensor circuit. For example, the first visible light sensor circuit 2015 can be shielded from receiving any of the second portion of visible emitted light passing through the unreactive portion 2010. Similarly, the second visible light sensor circuit 2020 can be shielded from receiving any of the first portion of the emitted visible light passing through the reactive portion 2005. Accordingly, the signals provided by the first and second visible light sensor circuits 2015 and 2020 may be more attributable to only that portion of the emitted visible light which passes through the associated portion of the color change material 100. The processor circuit 720 can access the first and second visible light sensor circuits 2015 and 2020 to provide the data set described herein with which the $CO_2$ level can be determined in some embodiments according to the invention. The embodiments illustrated by FIG. 23 can include various elements as described, for example, in FIG. 9 and can operate with any of the color change material 100 configurations and compositions described herein.

Figure 24:
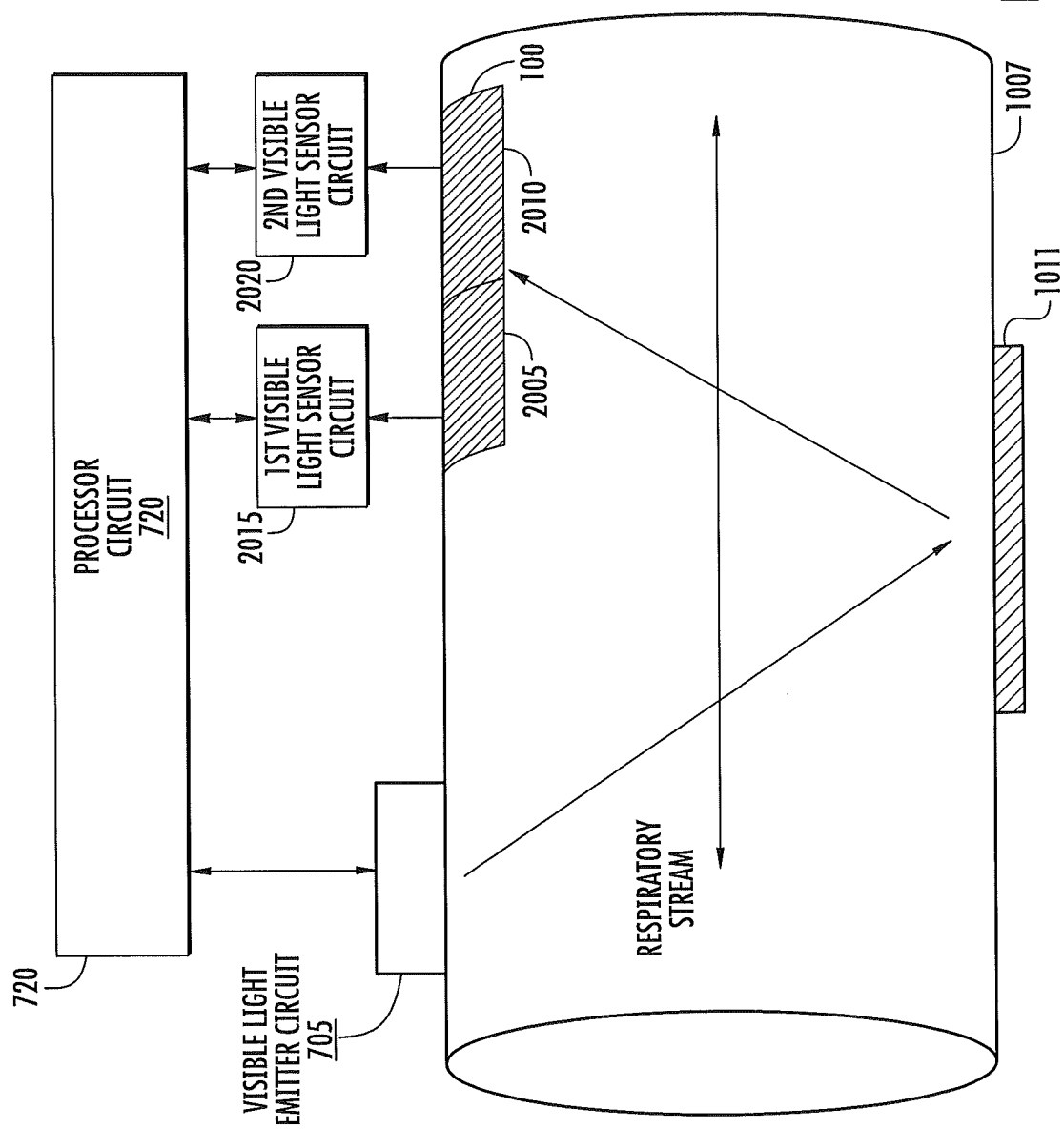
FIG. 24 is a schematic representation of a color change material included in a breathing circuit and exposed to electronically generated visible light and electronic sensing thereof in some embodiments according to the invention.

FIG. 24 is a schematic representation of a color change material included in a breathing circuit and exposed to electronically generated visible light and electronic sensing thereof in some embodiments according to the invention. According to FIG. 24, the processor circuit 720 operates the visible light emitter circuit 705 to provide emitted visible light to the reflector 1011 which reflects the visible emitted light onto the reactive and unreactive portions 2005 and 2010. The first portion of the emitted visible light passes through the reactive portion 2005 to impact the first visible light sensor circuit 2015. In contrast, the second portion of the visible emitted light passes through the unreactive portion 2010 to impact the second visible light sensor circuit 2020. As described above, the first and second visible light sensor circuits 2015 and 2020 are shielded from receiving any unintended portion of the emitted visible light. In operation, the processor circuit 720 can access the first and second visible light sensor circuits 2015 and 2020 to provide the data set upon which the $CO_2$ level can be determined in some embodiments according to the invention. The embodiments illustrated by FIG. 24 can include various elements as described, for example, in FIG. 8 and can operate with any of the color change material 100 configurations and compositions described herein.

Figure 25:
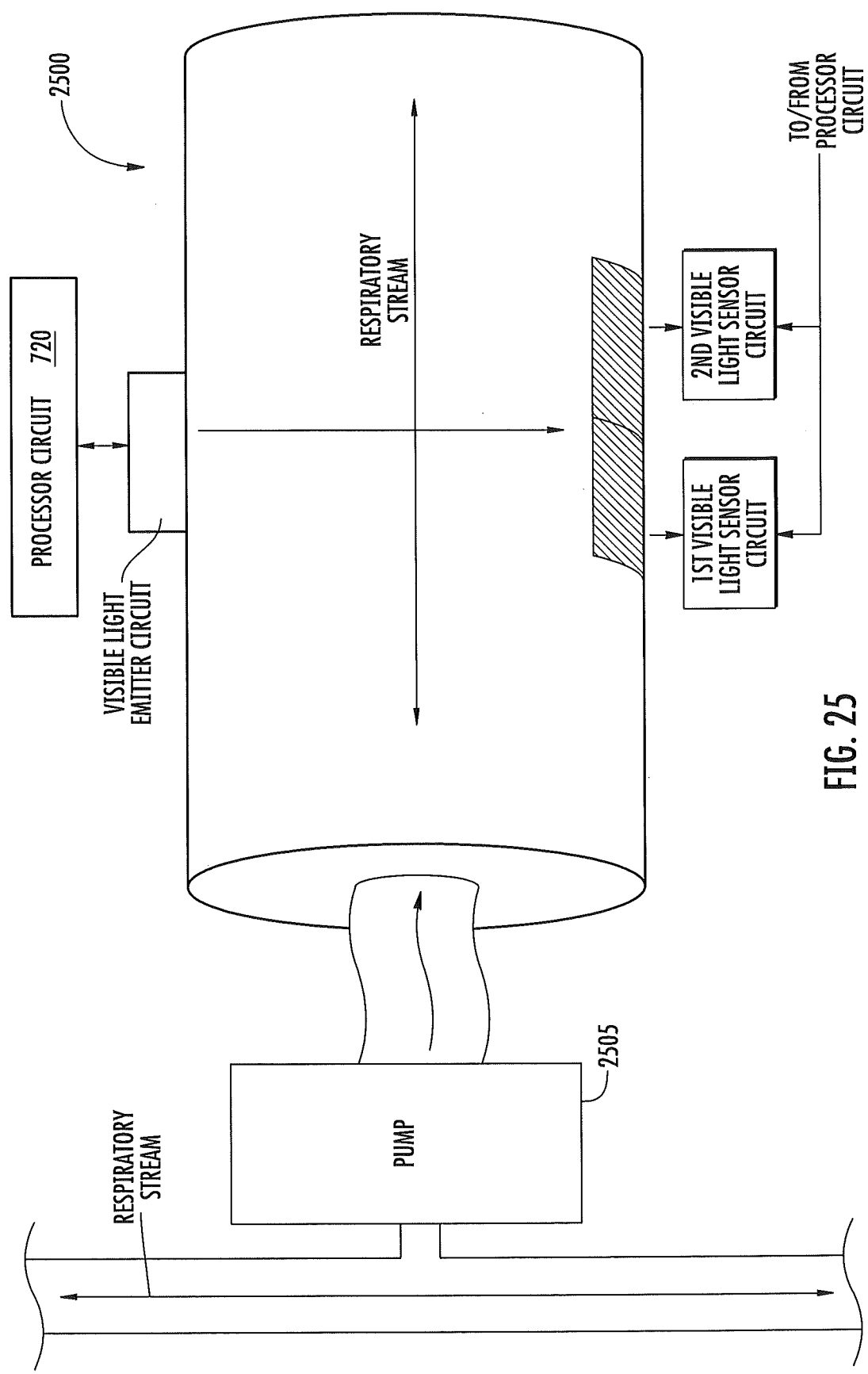
FIG. 25 is a schematic representation of a $CO_2$ detection system including a color change material in a breathing circuit and exposed to electronically generated visible light and electronic sensing thereof in a side stream configuration in some embodiments according to the invention.

FIG. 25 is a schematic representation of a $CO_2$ detection system 2500 including a color change material in a breathing circuit and exposed to electronically generated visible light and electronic sensing thereof in a side stream configuration in some embodiments according to the invention. According to FIG. 25, the system 2500 can include a processor circuit, visible light emitter circuit, color change material 100, and visible light sensor circuits as described herein. It will be further understood that although FIG. 25 illustrates the visible light emitter circuit and visible light sensor circuits on opposing sides of the breathing circuit, any configuration of visible light emitter circuits, visible light sensor circuits and color change material can be utilized in association with the side stream configuration shown in FIG. 25.

As further shown in FIG. 25, a pump 2505 is configured for coupling to the $CO_2$ detection system 2500 to provide the respiratory stream thereto. The pump 2505 is coupled to a main respiratory stream, from which the pump 2505 provides the respiratory stream to the $CO_2$ detection system 2500. It will be further understood that in some embodiments according to the invention, the $CO_2$ level detection system 2500 can be provided in a kit along with the pump 2505 or the $CO_2$ level detection system 2500 may be provided separately from the pump 2505. The $CO_2$ detection system 2500 illustrated by FIG. 25 can be used with any type of side stream configuration, such as that described in U.S. Patent Publication 2012/0215125, the entire disclosure of which is incorporated herein by reference.

Figure 26:
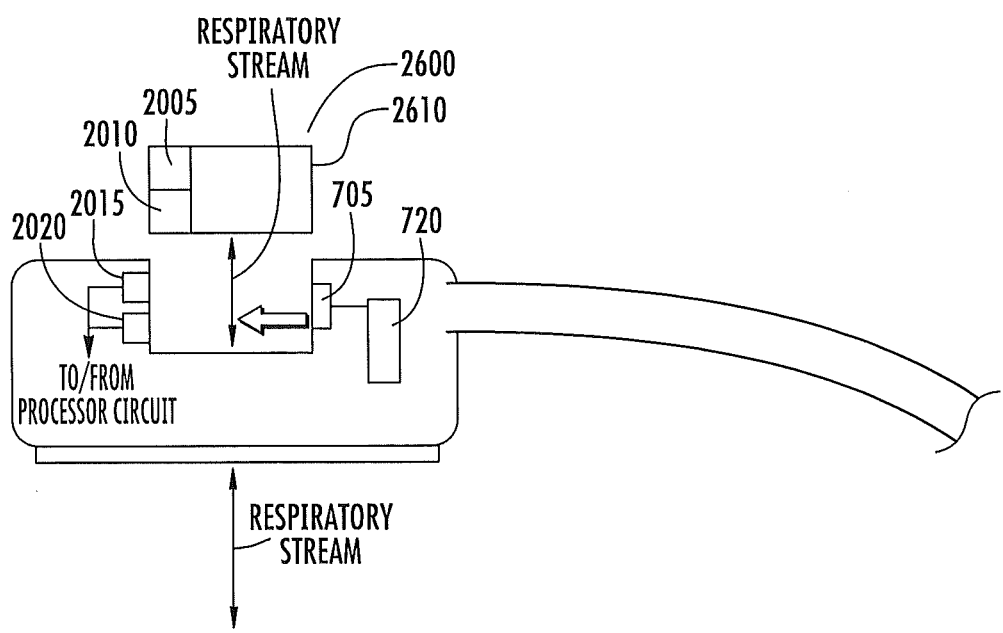
FIG. 26 is a schematic illustration of a $CO_2$ detection system including a color change material exposed to electronically generated visible light and electronic sensing thereof in an open breathing environment in some embodiments according to the present invention.

FIG. 26 is a schematic illustration of a $CO_2$ detection system 2600 including the color change material exposed to electronically generated visible light and electronic sensing thereof in an open breathing environment in some embodiments according to the present invention. According to FIG. 26, the $CO_2$ detection system 2600 is shown in the configuration where the visible light emitter circuit 705 is positioned on an opposing side of the breathing circuit relative to the visible light sensor circuits 2515 and 2520. It will be understood, however, that any configuration of $CO_2$ detection system described herein may be utilized in the open breathing environment. According to FIG. 26, the $CO_2$ detection system 2600 can be located proximate to a subject's nose or mouth (or any source of the subject's respiratory stream) so that the respiratory stream is provided to the $CO_2$ detection system 2600.

It will be understood that the $CO_2$ detection system 2600 can be provided proximate to the respiratory stream so that a portion of a housing 2605 of the $CO_2$ detection system 2600 can provide an open breathing circuit for the supply of the respiratory stream to the $CO_2$ detection system 2600. It will be further understood that a removable cartridge 2610 can house the reactive and unreactive portions of the color change material 100 such that when the removable cartridge 2610 is inserted into the housing 2605 of the $CO_2$ detection system, the respective portions are aligned with the appropriate visible light sensor circuit 2015, 2020. For example, when the removable cartridge 2610 is inserted into the housing 2605, the reactive portion 2005 is aligned with the first visible light sensor circuit 2015 and the unreactive portion 2010 is aligned with the second visible light sensor circuit 2020. In operation, the light emitted by the visible light emitter circuit 705 passes through the reactive and unreactive portions to impact the respective one of the visible light sensor circuits associated therewith. The processor circuit 720 can generate the data set from the signals provided by the sensor circuits 2015 and 2020 to determine the $CO_2$ level in accordance with embodiments of the invention as described herein. It will also be understood that other configurations described herein can be utilized in the open breathing environment shown in FIG. 26. Further, the embodiments illustrated by FIG. 26 can include various elements and operations as described, for example, in FIGS. 14-16 and can operate with any of the color change material 100 configurations and compositions described herein.

Figure 27:
FIGS. 27-31 are schematic representations of various configurations of color change materials at least partially included in a breathing circuit in some embodiments according to the invention.

FIGS. 27-31 illustrate various configurations of the color change material including reactive and unreactive portions relative to the breathing circuit 907 in some embodiments according to the invention. In FIG. 27, the color change material 100 includes the reactive portion 2005 and the unreactive portion 2010 as part of the same color change material 100 where a separator 2705 is located between the respective portions to shield the respective visible light sensor circuit associated with each of the portions of the color change material 100. Accordingly, the reactive portion 2005 may be treated with the color change indicator (and other materials as described herein) whereas the unreactive portion 2010 may be devoid of at least some components so that the color change exhibited by the unreactive portion when exposed to the same level of $CO_2$ is less than the reactive portion 2005. In some embodiments, the unreactive portion 2010 can be initially treated with the with the color change indicator, but may be quenched so as to become unreactive.

Figure 28:
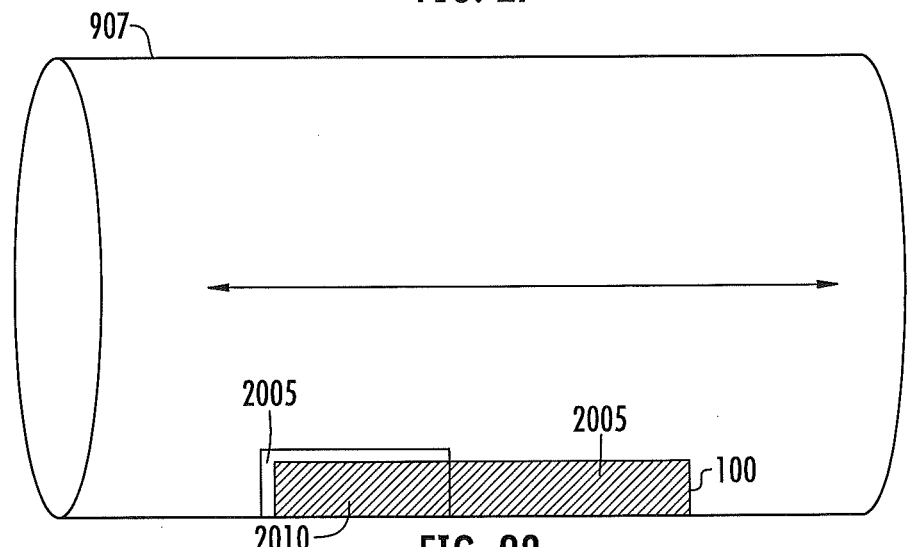

In FIG. 28, the color change material 100 can be treated so that both the reactive and unreactive portions 2005 and 2010 include the same color change indicators (and other components) such that the color change material may be a homogeneous strip. However, as further illustrated in FIG. 28, the unreactive portion 2010 may be coated with a material 2805 that isolates the unreactive portion 2010 from the $CO_2$ environment in the breathing circuit. Accordingly, the unreactive portion 2010 can include the material 2805.

Figure 29:
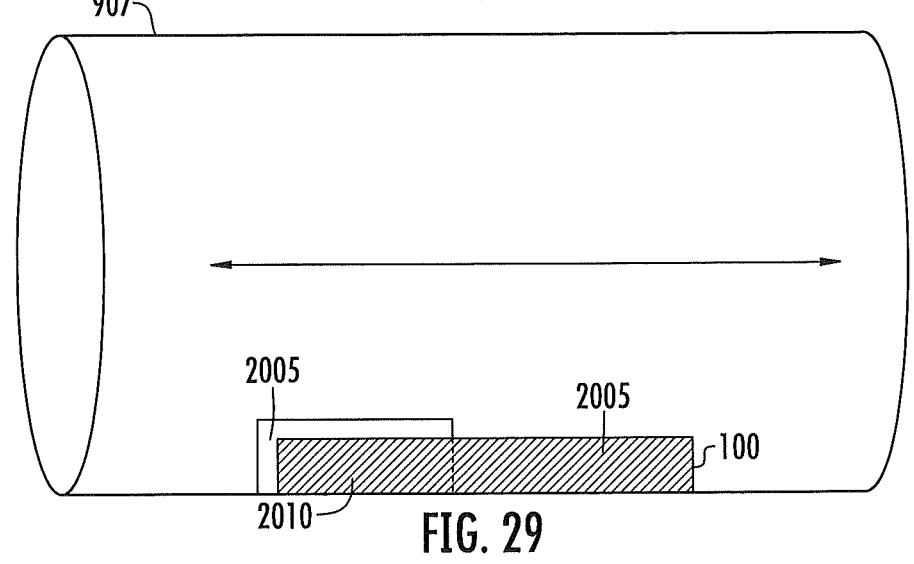

In FIG. 29, the color change material 100 includes the reactive portion 2005 and the unreactive portion 2010 where both portions are treated with the color change indicator and other components as described above in reference to FIG. 28. As further shown in FIG. 29, however, a housing 2905 is provided on a material wall of the breathing circuit 907 to isolate the unreactive portion 2010 from the respiratory stream.

Figure 30:
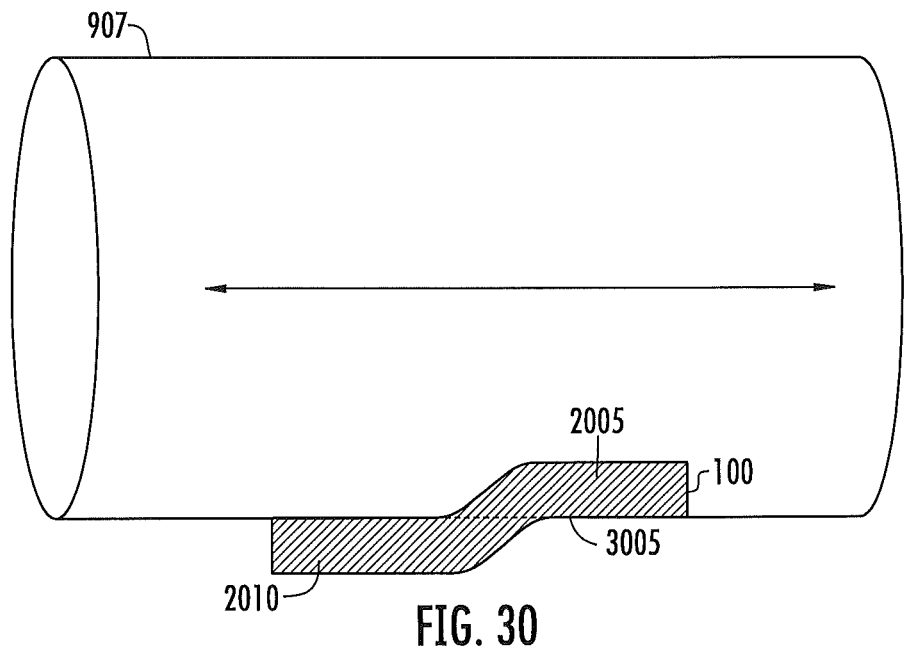

As shown in FIG. 30, the color change material includes the reactive portion 2005 and unreactive portion 2010 and, further, are provided as described above with reference to FIGS. 28 and 29 such that the color change material 100 is a homogenous strip of color change indicator and other components. As further shown in FIG. 30, however, the breathing circuit 907 includes a slot 3005 that allows the unreactive portion 2010 to be positioned outside the breathing circuit 907 so that it is isolated from the respiratory stream.

Figure 31:
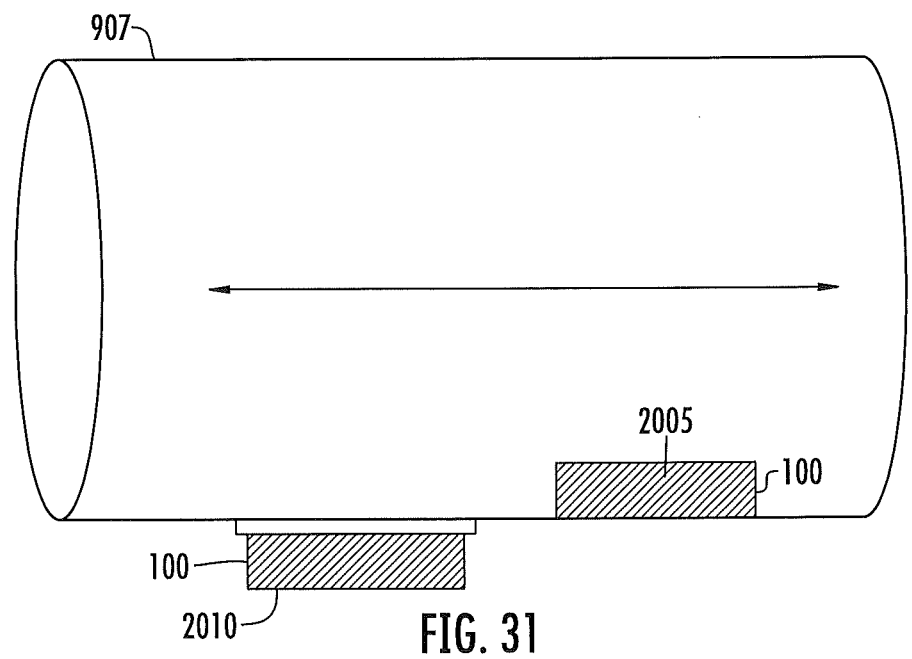

In FIG. 31, the color change material 100 is provided in two separate pieces wherein the reactive portion 2005 is located inside the breathing circuit 907 and exposed to the respiratory stream whereas the unreactive portion 2010 is located outside the breathing circuit 907 and is therefore isolated from the respiratory stream. In operation, the unreactive portion 2010 and the reactive portion 2005 are positioned so that the respective visible light sensor circuit are shielded. It will also be understood that any combination of configurations shown in FIGS. 27-31 may also be used in some embodiments according to the invention. It will be further understood that the color change material 100 configurations illustrated by FIGS. 27-31 can also be in any of the configurations shown in FIGS. 3-6 and can be used in any of the CO2 detection systems described herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present inventive subject matter. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

It will be understood that when an element or layer is referred to as being "on" another element or layer, the element or layer can be directly on another element or layer or intervening elements or layers may also be present. In contrast, when an element is referred to as being "directly on" another element or layer, there are no intervening elements or layers present. As used herein, the term "and/or" includes any and all combinations of one or more of the associated listed items.

Spatially relative terms, such as "below", "beneath", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation, in addition to the orientation depicted in the figures. Throughout the specification, like reference numerals in the drawings denote like elements.

Embodiments of the inventive subject matter are described herein with reference to plan and perspective illustrations that are schematic illustrations of idealized embodiments of the inventive subject matter. As such, variations from the shapes of the illustrations as a result, for example, of manufacturing techniques and/or tolerances, are to be expected. Thus, the inventive subject matter should not be construed as limited to the particular shapes of objects illustrated herein, but should include deviations in shapes that result, for example, from manufacturing. Thus, the objects illustrated in the figures are schematic in nature and their shapes are not intended to illustrate the actual shape of a region of a device and are not intended to limit the scope of the inventive subject matter.

The terminology used herein is for the purpose of describing particular embodiments only and is not intended to be limiting of the present inventive subject matter. As used herein, the singular forms "a", "an" and "the" are intended to include the plural forms as well, unless the context clearly indicates otherwise. It will be further understood that the terms "comprises" "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this present inventive subject matter belongs. It will be further understood that terms used herein should be interpreted as having a meaning that is consistent with their meaning in the context of this specification and the relevant art and will not be interpreted in an idealized or overly formal sense unless expressly so defined herein. The term "plurality" is used herein to refer to two or more of the referenced item.

It will be understood that, as used herein, the term light emitting device may include a light emitting diode, laser diode and/or other semiconductor device which includes one or more semiconductor layers, which may include silicon, silicon carbide, gallium nitride and/or other semiconductor materials, a substrate which may include sapphire, silicon, silicon carbide and/or other microelectronic substrates, and one or more contact layers which may include metal and/or other conductive layers.

As will be appreciated by one skilled in the art, aspects of the present disclosure may be illustrated and described herein in any of a number of patentable classes or contexts including any new and useful process, machine, manufacture, or composition of matter, or any new and useful improvement thereof. Accordingly, aspects of the present disclosure may be implemented entirely hardware, entirely software (including firmware, resident software, microcode, etc.) or combining software and hardware implementation that may all generally be referred to herein as a "circuit," "module," "component," or "system." Furthermore, aspects of the present disclosure may take the form of a computer program product comprising one or more computer readable media having computer readable program code embodied thereon.

Any combination of one or more computer readable media may be used. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks.

These computer program instructions may also be stored in a computer readable medium that when executed can direct a computer, other programmable data processing apparatus, or other devices to function in a particular manner, such that the instructions when stored in the computer readable medium produce an article of manufacture including instructions which when executed, cause a computer to implement the function/act specified in the flowchart and/or block diagram block or blocks. The computer program instructions may also be loaded onto a computer, other programmable instruction execution apparatus, or other devices to cause a series of operational steps to be performed on the computer, other programmable apparatuses or other devices to produce a computer implemented process such that the instructions which execute on the computer or other programmable apparatus provide processes for implementing the functions/acts specified in the flowchart and/or block diagram block or blocks.

In the drawings and specification, there have been disclosed typical preferred embodiments of the inventive subject matter and, although specific terms are employed, they are used in a generic and descriptive sense only and not for purposes of limitation, the scope of the inventive subject matter being set forth in the following claims.

What is claimed:

1. A composition comprising:
    a dye present in an amount of about 0.001% to about 0.1% by weight of the composition;
    a buffer present in an amount of about 0.5% to about 10% by weight of the composition;
    an alkaline material present in an amount of about 0.1% to about 10% by weight of the composition;
    a nitrogen containing compound configured to provide an increase in a colorific response present in an amount of about 0.01% to about 2% by weight of the composition; and
    a water-attractive component present in an amount of about 5% to about 50% by weight of the composition.

2. The composition of claim 1, further comprising an antimicrobial additive present in an amount of about 1 ppm to about 1000 ppm.

3. The composition of claim 1, further comprising a surface modifying additive present in an amount of about 0.1% to about 1% by weight of the composition.

4. The composition of claim 1, wherein said nitrogen containing compound is chosen from an amine, a quaternary ammonium compound, an amino acid, an amino acid derivative, and any combination thereof.

5. A color change material comprising:
    a substrate; and
    the color change composition of claim 1,
    wherein said color change composition is in contact with at least a portion of the said substrate.

6. The color change material of claim 5, wherein said color change material is dry or partially hydrated.

7. The color change material of claim 5, wherein said substrate is optically transmissive.

8. A carbon dioxide indicator comprising:
    a color change material comprising the color change composition of claim 1, wherein said color change material is responsive to carbon dioxide; and
    a control material, wherein said control material is substantially non-responsive to carbon dioxide.

9. The carbon dioxide indicator of claim 8, wherein said color change material and said control material are configured to be exposed to substantially the same conditions.

10. The carbon dioxide indicator of claim 8, wherein said color change material is configured to change from a first color to a second color and return to said first color in response to contact with at least one carbon dioxide concentration.

11. The carbon dioxide indicator of claim 8, wherein said color change material is configured to change from a first color to a second color and return to said first color about 1 to about 60 times per minute in response to contact with at least two consecutive carbon dioxide concentrations.

12. The carbon dioxide indicator of claim 8, wherein in operation, said color change material and said control material are substantially the same color at a first $CO_2$ concentration prior to contact with a second $CO_2$ concentration having a greater $CO_2$ concentration.

13. The carbon dioxide indicator of claim 8, wherein said control material comprises a dye and is configured to be non-responsive to carbon dioxide by quenching said dye.

14. The carbon dioxide indicator of claim 8, wherein at least of a portion of said color change material is configured to provide a first color of a particular value and hue and said control material is printed to a second color that is substantially the same value and hue as the first color.

15. The composition of claim 1, wherein the composition, when applied to a portion of a substrate, is configured to change the portion of the substrate from a first color to a second color and return the portion of the substrate to the first color about 1 to about 60 times per minute in response to contact with at least two consecutive carbon dioxide concentrations.

16. The composition of claim 15, wherein the substrate is filter paper.

17. The composition of claim 1, wherein the composition has a pH of about 8 to about 10.

18. A composition comprising:
   metacresol purple present in an amount of about 0.001% to about 0.1% by weight of the composition;
   a buffer present in an amount of about 0.5% to about 10% by weight of the composition;
   an alkaline material comprising a carbonate, the alkaline material present in an amount of about 0.1% to about 10% by weight of the composition;
   monoethanolamine present in an amount of about 0.01% to about 2% by weight of the composition; and
   a water-attractive component present in an amount of about 5% to about 50% by weight of the composition.

19. The composition of claim 18, wherein the composition, when applied to a portion of a substrate, is configured to change the portion of the substrate from a first color to a second color and return the portion of the substrate to the first color about 1 to about 60 times per minute in response to contact with at least two consecutive carbon dioxide concentrations.

20. The composition of claim 19, wherein the substrate is filter paper.

21. A carbon dioxide indicator comprising:
   a color change material comprising a substrate and a color change composition that is in contact with at least a portion of said substrate, wherein said color change material is responsive to carbon dioxide; and
   a control material, wherein said control material is substantially non-responsive to carbon dioxide,
   wherein said substrate comprises filter paper and said color change material comprises:
      metacresol purple present in an amount of about 0.001% to about 0.1% by weight of the composition;
      a buffer present in an amount of about 0.5% to about 10% by weight of the composition;
      an alkaline material comprising a carbonate, the alkaline material present in an amount of about 0.1% to about 10% by weight of the composition;
      monoethanolamine present in an amount of about 0.01% to about 2% by weight of the composition; and
      a water-attractive component present in an amount of about 5% to about 50% by weight of the composition.

* * * * *